US006552103B1

(12) United States Patent
Bertozzi et al.

(10) Patent No.: US 6,552,103 B1
(45) Date of Patent: Apr. 22, 2003

(54) BIOMIMETIC HYDROGEL MATERIALS

(75) Inventors: Carolyn Bertozzi, Albany, CA (US); Ravindranath Mukkamala, Houston, TX (US); Oing Chen, Albany, CA (US); Hopin Hu, Albuquerque, NM (US); Dominique Baude, Creteil (FR)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/574,938

(22) Filed: May 19, 2000

Related U.S. Application Data

(62) Division of application No. 09/145,507, filed on Sep. 2, 1998, now Pat. No. 6,107,365.
(60) Provisional application No. 60/057,444, filed on Sep. 3, 1997.

(51) Int. Cl.[7] .................................................. G02C 7/04
(52) U.S. Cl. ...................... 523/106; 523/108; 525/54.2; 524/916; 351/160 R; 264/1.1; 264/1.32; 264/1.7
(58) Field of Search ................................. 523/106, 108; 351/160 R; 264/1.1, 1.32, 1.7; 524/916; 525/54.2

(56) References Cited

U.S. PATENT DOCUMENTS

| | | | | |
|---|---|---|---|---|
| 4,163,609 A | | 8/1979 | Neefe | 351/160 |
| 5,093,447 A | | 3/1992 | Novicky | 526/270 |
| 5,135,965 A | | 8/1992 | Menashe Tehan | 523/106 |
| 5,157,093 A | * | 10/1992 | Harisiades et al. | 528/69 |
| 5,185,466 A | | 2/1993 | Kozulic et al. | 564/208 |
| 5,214,452 A | * | 5/1993 | Kossmehl et al. | 351/160 R |
| 5,292,514 A | | 3/1994 | Capecchi et al. | 424/422 |
| 5,410,016 A | | 4/1995 | Hubbell et al. | 528/354 |
| 5,690,953 A | * | 11/1997 | Molock et al. | 523/106 |
| 5,939,466 A | * | 8/1999 | Bachmann et al. | 523/106 |

FOREIGN PATENT DOCUMENTS

| | | | |
|---|---|---|---|
| EP | 86304286.7 | 6/1986 | G02B/1/04 |
| EP | 92311647.9 | 12/1992 | 5/14 |
| EP | 95810079.4 | 2/1995 | 37/16 |
| EP | 98120257.5 | 10/1998 | 1/4 |

OTHER PUBLICATIONS

M. Morra et al, On The Wettability of Poly(2–Hydroxyethylmethacrylate), Journal of Colloid and Interface Science, 149/1:84–91 (Mar. 1, 1992).

Takashi Miyata, et al, Protein Adsorption On A Copolymer Having Pendant Monosaccharide Groups. Relationship Between Surface Free Energy and Protein Adsorption, Macromol. Chem. Phys., 195:3597–3607 (1994).

Weisz, et al, Hepatocyte Adhesion to Carbohydrate–Derivatized Surfaces, The Journal of Cell Biology, 115/2:485–493 (Oct. 1991).

Biessen et al, Specific Targeting of the Antiviral Drug 5–Iodo 2'–deoxyuridine To The Parenchymal Liver Cell Using Lactosylated Poly–L–lysine, Journal of Hepatology, 21:806–815 (1994).

Manning et al, Synthesis of Sulfated Neoglycopolymers: Selective P–Selectin Inhibitors, J. Am. Chem. Soc., 119:3161–3162, (1997).

Matrosovich, et al, Synthetic Polymeric Sialoside Inhibitors of Influenza Virus Receiptor–binding Activity, Federal of European Biochemical Societies, 272/1,2:209–212 (Oct. 1990)).

Roy et al, New Strategy in Glycopolymer Syntheses. Preparation of Antigenic Water–Soluble Poly(acrylamide–co-p–acrylamidophenyl Beta–lactoside, Bioconjugate Chem., 3:256–261 (1992).

Gamian, et al, Inhibition of Influenza A Virus Hemagglutinin and Induction of Interferon by Synthetic Sialylated Glyconconjugates, Can. J. Microbiol., 37 (1991).

Joachim Klein, et al., Synthesis of Some Poly(vinylsaccharide)s of the Amide Type And Investigation Of Their Solution Properties, *Makromol. Cheml*, 188/6:1217–1232 (1987).

Von H.–G Batz, et al., Pharmakologisch Aktive Polymere, *Arzneim.–Forsch./Drug Res.*, 27/II:1884–1888 (1977).

* cited by examiner

*Primary Examiner*—Peter Szekely
(74) *Attorney, Agent, or Firm*—Hana Verny

(57) ABSTRACT

Novel biomimetic hydrogel materials and methods for their preparation. Hydrogels containing acrylamide-functionalized carbohydrate, sulfoxide, sulfide or sulfone copolymerized with a hydrophilic or hydrophobic copolymerizing material selected from the group consisting of an acrylamide, methacrylamide, acrylate, methacrylate, vinyl and a derivative thereof present in concentration from about 1 to about 99 wt %. and methods for their preparation. The method of use of the new hydrogels for fabrication of soft contact lenses and biomedical implants.

9 Claims, 14 Drawing Sheets

BIOMIMETIC HYDROGEL MATERIALS

This is a divisional application of the U.S. application Ser. No. 09/145,507 filed on Sep. 2, 1998, now U.S. Pat. No. 6,107,365, which claims benefit of provisional application No. 60/057,444, filed Sep. 3, 1997.

NOVEL BIOMIMETIC HYDROGEL MATERIALS

The United States Government has certain rights in this invention pursuant to Contract DE-AC03-76SF00098 between the United States Department of Energy and the University of California.

BACKGROUND OF THE INVENTION

This invention concerns novel biomimetic hydrogel materials and methods for their preparation. In particular, the invention concerns hydrogels containing acrylamide-functionalized carbohydrate, sulfoxide, sulfide or sulfone copolymerized with hydrophilic or hydrophobic copolymerizing material, such as acrylamide, methacrylamide, acrylate, methacrylate or vinyl or their derivatives such as 2-hydroxyethyl methacrylate, and methods for their preparation. The invention also concerns the use of the new hydrogels for fabrication of soft contact lenses and biomedical implants. Additionally, the invention concerns novel acrylamide-functionalized carbohydrates, sulfoxide, sulfide and sulfone.

BACKGROUND AND RELATED DISCLOSURES

Hydrogel polymers have found widespread use in the biomedical materials industry as implant materials in both vascular and tissue environments. They are readily fabricated into a variety of morphologies and can exhibit a range of properties depending on their constituents. Their defining feature is the ability to absorb and hold water, a property which is dominated by the presence of hydrophilic groups in the bulk material.

Biological hydrogels serving various functions are known in nature. For example, during the process of bone growth collagen fibers form hydrogels upon which mineral nucleation takes place. The carbohydrate layer of the cell surface forms a hydrogel-like matrix that protects and hydrates the cell surface. The sophisticated structures of this nature fulfill various functions in complex biological processes.

By comparison, the hydrogel polymers that are manufactured for biomedical applications bear little functionality.

Polymers having pendant sugar moieties know as "glycopolymers" (*Bioconj. Chem.*, 3:256 (1992) have attracted much interest in recent years, largely as scaffolds for the multivalent display of biologically important carbohydrate molecules. These glycopolymers have been used as potent inhibitors of viral-host cell attachment and leukocyte-endothelial cell adhesion (*FEBS*, 272:209 (1990); *Can. J. Microbiol.*, 37:233 (1991); *J. Am. Chem. Soc.*, 119:3161 (1997). Glycopolymers have also been explored as vehicles for targeted drug and gene delivery (*J. Hepatology*, 21:806 (1994), and as artificial substrates for cell adhesion (*J. Cell Biol.*, 115:485 (1991). The suitability of glycopolymers as biocompatible implant materials has been relatively unexplored and is limited to a few examples described, for example, in *Microbiol. Chem. Phys.*, 195:3597 (1994).

For polymers used as biocompatible implant materials, their properties, particularly the surface composition, are of great importance. Efforts include introducing biocompatible components into the bulk system and on their surface. Studies described, for example, in *J. Colloid Interface Sci.*, 149:84 (1992) have shown that copolymers with a pendant glucose unit in the bulk or surfaces with covalently bound neutral polysaccharides demonstrate the reduction of platelet adhesion and protein adsorption.

The primary objective of this invention is thus to provide novel biomimetic, biocompatible hydrogel materials of modified surface having the high hydrophilicity, wettability and low protein adsorption suitable for use as biomedical implants.

All U.S. patents and patent applications cited and referred to herein are hereby incorporated by reference.

SUMMARY

One aspect of the current invention is a hydrogel material prepared by copolymerization of hydrophilic or hydrophobic copolymerization material with acrylamide-functionalized carbohydrate monomers.

Another aspect of the current invention is a hydrogel material wherein the carbohydrate monomer is selected from the group consisting of N-methyl-N-β-rhamnosyl acrylamide, N-[3-(2-N-ethyl propenamido)thiopropyl]-β-N-xylosyl acetamide, N-acryloyl-N-methyl-D-glucamine, N-acryloyl-D-glucamine and N-acryloyl-N-(4-(3,6,9-trioxa) decyloxybenzyl)-D-glucamine.

Still another aspect of the current invention is an acrylamide-functionalized carbohydrate selected from the group consisting of N-methyl-N-β-rhamnosyl acrylamide, N-[3-(2-N-ethyl propenamido)thiopropyl]-β-N-xylosyl acetamide, N-acryloyl-N-methyl-D-glucamine, N-acryloyl-D-glucamine and N-acryloyl-N-(4-(3,6,9-trioxa) decyloxybenzyl)-D-glucamine.

Still another aspect of the current invention is a method for synthesis of hydrogel comprising an acrylamide-functionalized carbohydrate monomer.

Yet another aspect of the current invention is a hydrogel material prepared by copolymerization of copolymerization material with sulfoxide, sulfide or sulfone.

Still yet another aspect of the current invention is a method for preparation of sulfoxide, sulfide or sulfone containing hydrogels.

Still yet another aspect of the current invention is a hydrogel acrylamide containing carbohydrate, sulfoxide, sulfide or sulfone useful for production of improved soft contact lenses and other biomedical implants.

Still yet another aspect of the current invention is an acrylamide-functionalized sulfoxide, sulfide or sulfone.

BRIEF DESCRIPTION OF DRAWINGS

FIG. 10 shows protein adsorption on various commercial soft contact lenses and on the hydrogels containing 20% of monomers 3 and 4.

DEFINITIONS

Figure 1:
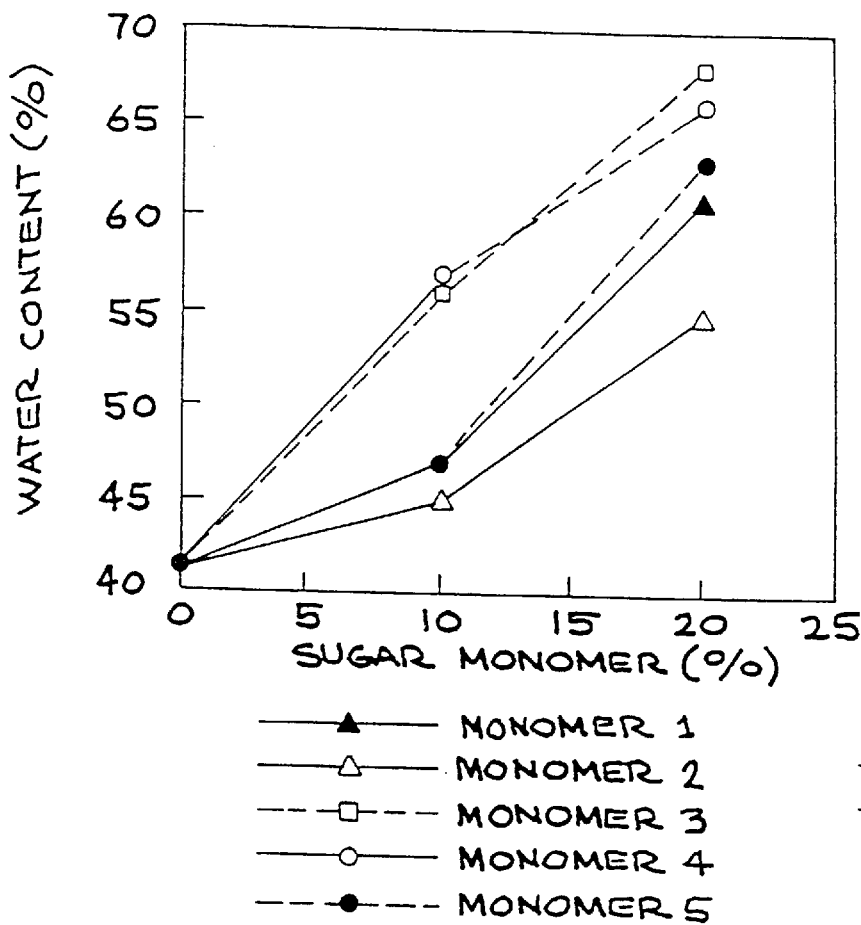
FIG. 1 shows an equilibrium water content (wt %) of hydrated HEMA-carbohydrate hydrogels as a function of percentage of the carbohydrate monomer 1 (-▲-), 2 (-Δ-), 3 (-□-), 4 (-○-), and 5 (-●-).

As used herein:

"Hydrogel" means a copolymer comprising HEMA copolymerized with the carbohydrate, sulfoxide, sulfide or sulfone monomer.

"HEMA" means 2-hydroxyethyl methacrylate.

"EGDMA" means ethyleneglycol dimethylacrylate.

"Functionalized" means derivatized with acrylamide.

"Sugar monomer" or "carbohydrate monomer" means functionalized carbohydrates with acrylamide.

"Copolymer" means carbohydrate monomer or sulfoxide, sulfide or sulfone functionalized with acrylamide copolymerized with HEMA.

"ATF" means artificial tear fluid.

DETAILED DESCRIPTION OF THE INVENTION

The current invention discloses a new class of biomimetic hydrogel polymers bearing pendant carbohydrate, sulfoxide, sulfide or sulfone groups. The hydrogels are prepared by the copolymerization of a hydrophilic or hydrophobic matrix copolymerizing material selected from the group consisting of acrylamide, methacrylamide, acrylate, methacrylate, siloxane and vinyl or their derivatized forms 2-hydroxyethylacrylate (HEMA), N-vinyl-pyrrolidone (NVP), methyl methacrylate (MMA), methacrylic acid (AcM), 1,2-dihydroxy-propyl methacrylate (DPMA), glycerol methacrylate (GMA) or N,N-dimethyl acrylamide (DMA) with acrylamide functionalized carbohydrate monomers or with acrylamide functionalized sulfoxide, sulfide or sulfone. The new hydrogels have improved biocompatibility, low immunogenicity, and increased equilibrium water content, water retention, surface hydrophilicity and reduced protein adsorption and binding activity. The new hydrogels are suitable for use in biomedical implant applications in general and commercial soft contact lenses applications in particular.

The invention additionally discloses the acrylamide-functionalized carbohydrates, sulfoxide, sulfide and sulfone.

I. Carbohydrate Hydrogels

Carbohydrate hydrogels of the invention are polymers comprising acrylamide-functionalized carbohydrate monomers copolymerized with the hydrophilic or hydrophobic matrix copolymerizing materials selected from the group consisting of acrylamide, methacrylamide, acrylate, methacrylate, siloxane and vinyl or their derivatized forms, such as N-vinyl-pyrrolidone (NVP), methyl methacrylate (MMA), methacrylic acid (AcM), 1,2-dihydroxy-propyl methacrylate (DPMA), glycerol methacrylate (GMA) or N,N-dimethyl acrylamide (DMA), siloxane or glycerol methacrylate, preferably with hydroxyethyl methacrylate (HEMA). Because of its easy handling HEMA was selected as a representative copolymerizing material. However, all other above listed materials are conveniently exchangeable with HEMA and in the novel hydrogels they function in substantially the same way as HEMA.

In a physiological environment, HEMA portion of the new hydrogel possesses physical strength and relative chemical inertness, whereas carbohydrate moiety of the new hydrogel possesses favorable hydration properties, low immunogenicity and ubiquitous presence on the surface of the mammalian cells. Carbohydrate and HEMA containing hydrogels combine all the above mentioned properties.

High hydrophilicity, wettability and equilibrium water content of the novel hydrogel polymers result in high oxygen permeability and various other biologically important functionalities which give these hydrogels potential to become much desired biocompatible materials.

A. Acrylamide-Functionalized Carbohydrates

1. Compounds Identification

The carbohydrate moiety of the novel hydrogel of the invention comprises functionalized carbohydrates, in particular, carbohydrates functionalized with polymerizable acrylamide groups.

Acrylamide-functionalized carbohydrate monomers of the invention are represented by carbohydrate monomers shown in Chart 1, wherein the monomer 1 is N-methyl-N-β-rhamnosyl acrylamide (1); monomer 2 is N-[3-(2-N'-ethyl propenamido)thiopropyl]-β-N-xylosyl acetamide (2); monomer 3 is N-acryloyl-D-glucamine (3); monomer 4 is N-acryloyl-N-methyl-D-glucamine; and monomer 5 is N-acryloyl-N-(4(3,6,9-trioxa) decyloxybenzyl)-D-glucamine (5).

SCHEME 1

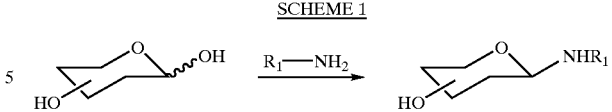

CHART 1

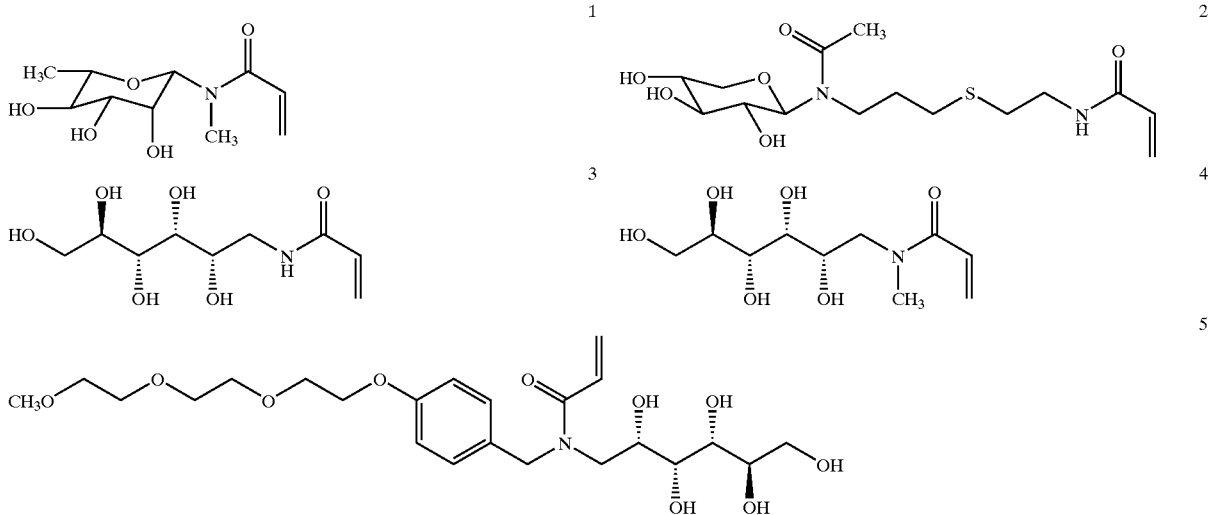

Other compounds, such as other carbohydrates similarly functionalized with acrylamide or acrylate esters or any other agent conferring the same or similar functionality on these compounds may be used to substitute for the monomers listed above.

Polymerizable carbohydrate acrylamide compounds falling within the scope of this invention have a general formula

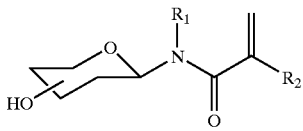

wherein $R_1$ is alkyl, cycloalkyl or aryl and $R_2$ is hydrogen, alkyl, cycloalkyl or aryl.

The compound comprises any monosaccharide or oligosaccharide in which the reducing terminal pyranose or furanose unit is linked to the acrylamide group through a glycosamine.

2. Synthesis of Derivatized Glycosamines

Synthesis of derivatized carbohydrates is based on the intermediacy of glycosamines produced by incubation of free reducing sugars with simple primary alkylamines according to *Angew. Chem. Int. Ed. Engl.*, 30:1611 (1991). This approach allows derivatization of sugars at their reducing end. Generic reaction for preparation of acrylamide-functionalized carbohydrates is shown in Scheme 1.

-continued

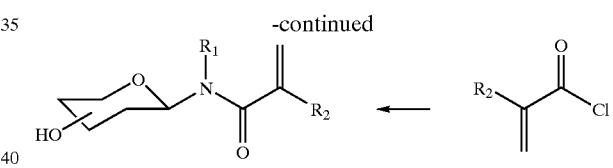

wherein $R_1$ is and $R_2$ is hydrogen, alkyl, cycloalkyl or aryl.

The saccharide is first treated with an amine comprising $R_1$ group. This step is known in the art. In the second step, when $R_2$ is hydrogen, the amine is acylated with the acrylate group, when $R_2$ is methyl, the amine is treated with methacrylate group, and when $R_2$ is alkyl, cycloalkyl or aryl, the amine is treated with other acrylate derivatives.

Two methods were successfully utilized for preparation of acrylamide functionalized carbohydrate monomers 1 and 2. These methods are illustrated in Schemes 2 and 3. One step synthetic method was used for synthesis of monomers 3 and 4. The monomer 5 was prepared by functionalization with a triethylene glycol group.

i. L-Rhamnose Acrylamide Method

The first method, exemplified by the synthesis of L-rhamnose-acrylamide, monomer 1, described in Example 2, involves treatment of the free sugar, with methylamine to form rhamnosylamine, compound 6, exclusively in β-configuration. The detailed procedure of the method is described in Example 3. The monomer 1 is prepared according to Scheme 2.

SCHEME 2

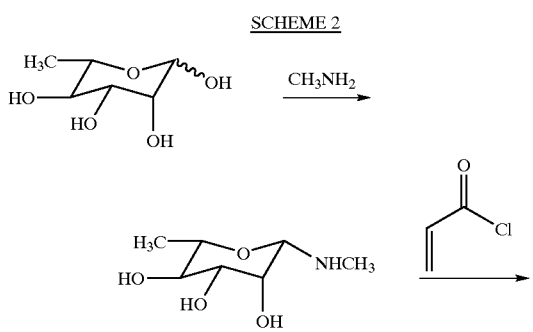

The L-rhamnose acrylamide reaction is simple, proceeds without prior purification and involves reacting the glycosamine intermediate with acryloyl chloride under mild basic conditions to afford the desired acrylamide derivative.

ii. Thioether-based Linker Method

The second method utilizes modified procedure described in *Mater. Res. Soc. Symp. Proc.*, 394:187 (1995). The method involves insertion of a short thioether-based linker between the carbohydrate moiety and polymerizable acrylamide group represented in this instance by xylose derivative, compound 2. The detailed method is described in the example 5. The reaction is illustrated in Scheme 3.

of monosaccharides and higher order polysaccharides, either synthetic and derived from natural sources, such as glycoproteins found in serum or tissues, or oligosaccharides from plants, insects or animals, etc.

All monosaccharide and polysaccharides suitable for preparation of the hydrogels of the invention are included to be within the scope of the invention.

iii. One-step Method

Polymerizable derivatives monomers 3 and 4, possessing open chain alditol groups, were synthesized in one step from commercially available D-glucamine compound 10 and N-methyl-D-glucamine compound 11, respectively, yielding monomers 3 and 4. The method is illustrated in Scheme 4.

SCHEME 4

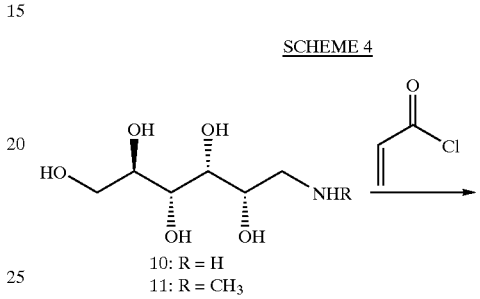

10: R = H
11: R = CH₃

SCHEME 3

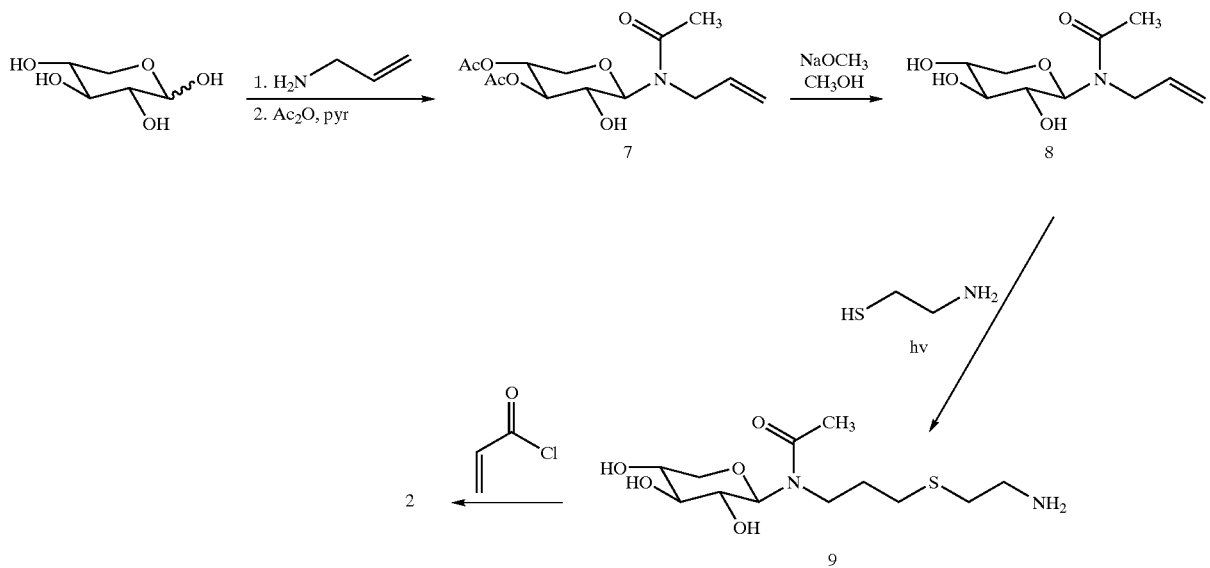

As seen in Scheme 3, free D-xylose is treated with neat allylamine overnight, to yield an intermediate xylosylallylamine derivative. This derivative, which hydrolyzes readily in the presence of water, is acetylated with acetic anhydride (Ac₂O) in pyridine (pyr) to give a stable acetylated product, compound 7, and then de-O-acetylated to give stable glycosylamide compound 8. Anti-Markovnikov free radical addition of 2-aminoethanethiol to the alkene is effected by exposure to UV light in aqueous buffer to provide compound 9. Selective acryloylation of the amino group of the compound 9 is achieved by reaction with acryloyl chloride under mild basic conditions, affording the desired polymerizable target monomer 2.

Both of these methods for the specific attachment of acrylamide groups to sugars are readily adapted to a range -continued

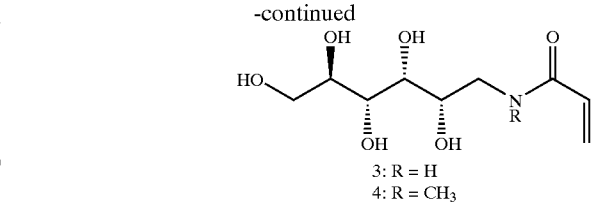

3: R = H
4: R = CH₃ iv. Functionalization with Triethyleneglycol

A polymerizable glucamine derivative, monomers 5, was functionalized with triethyleneglycol group according to Scheme 5.

SCHEME 5

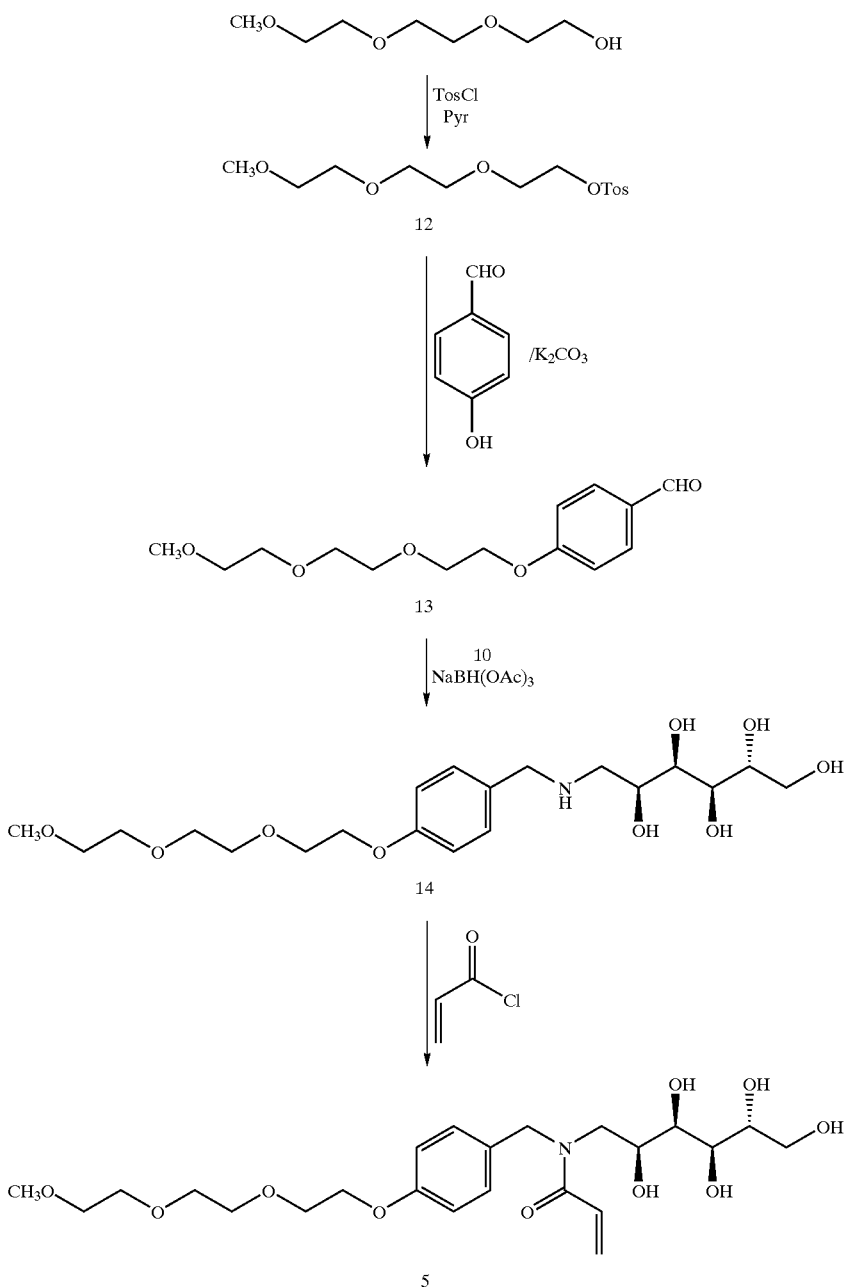

Monomer 5 was prepared as depicted in Scheme 5. Triethyleneglycol monomethylether was converted to the corresponding tosylate compound 12 and then reacted with 4-hydroxybenzaldehyde under basic conditions to afford adduct 13. Reductive amination of aldehyde compound 13 with 1-amino-1-deoxy-D-sorbitol compound 10 gave compound 14, which was acylated with acryloyl chloride to afford polymerizable derivative monomer 5.

3. Copolymerization of Carbohydrates with HEMA

Poly(2-hydroxyethyl methacrylate) (HEMA) hydrogels, which are endowed with many favorable properties for biomedical applications, were used as a representative system for preparation of hydrogels containing carbohydrate acrylamide monomers. In the novel hydrogels of the invention, HEMA is a representative and may be substituted with matrix copolymerizing material selected from the group consisting of acrylamide, methacrylamide, acrylate, methacrylate, siloxane and vinyl or their derivatized forms, such as 2-hydroxyethyl acrylate (HEMA), N-vinylpyrrolidone (NVP), methyl methacrylate (MMA), methacrylic acid (AcM), 1,2-dihydroxypropyl methacrylate (DPMA), glycerol methacrylate (GMA) or N,N-dimethyl acrylamide (DMA) or any other matrix copolymerizing substance.

The novel hydrogels were prepared by copolymerization of HEMA or the other material, as listed above, with a carbohydrate moiety, preferably with those carbohydrates described above as monomers 1–5, present in concentration from about 1 to about 99 wt %, preferably about 5 to about 40 wt %, most preferably about 10 to 20 wt % optionally in a presence of a cross-linker, in amount from about 0.1 to about 2%, preferably about 1%.

Copolymerization of HEMA with a carbohydrate monomer was achieved by reacting HEMA in concentration from about 1 to about 99 wt %, preferably about 60 to 90 wt %, most preferably about 75–80 wt % with the carbohydrate monomer in concentration from about 1 wt % to about 99 wt %, preferably about 5 to about 40 wt %, most preferably about 20 to 40 wt %, in the presence of cross-linker, preferably ethylene glycol dimethacrylate (EGDMA) present at about 0.01–2%, preferably, about 1%. The reaction is able to proceed without presence of a solvent, or is performed in the presence of water and/or an aqueous or organic solvent, such as ethylene, glycol or DMSO. An initiator, such as ammonium persulfate (($NH_4)_2S_2O_8$) about 400 mg/mL, sodium bispersulfate ($Na_2S_2O_5$), about 150 mg/mL, or any other initiator of the polymerization reaction may be added. The reaction proceeds at room temperature or with mild heat, and typically requires no longer time than overnight.

Prior to polymerization, the solution can be poured into a shape required for medical implant or poured between two glass plates to form hydrogel film of thickness corresponding to the space between the two glass plates. Detailed description of preparation of copolymers is in Example 11.

Additionally, other compounds, both inert or confirming certain biologically important characteristics and/or changing the properties and functionalities of the hydrogels may be added to the carbohydrate monomer and HEMA. These may be bioactive proteins, peptides, lipids, amino acids, or ethyleneglycol, inert compounds or other functional substances such as, antibacterials, pharmaceuticals, a dye for color lenses, etc.

It is one of the advantages of this invention that by changing the ratio of carbohydrate to HEMA, by selecting a different carbohydrate or by adding other components, the hydrogel material may be specifically designed to acquire the properties desired for a particular use.

In order to demonstrate and confirm the improved properties of the new hydrogels, the effect of carbohydrate content on the hydrophilicity. of polymers, water content, protein binding, etc., was determined. For that purpose, copolymers with various percentages of carbohydrates from 0 wt %, 5 wt %, 10 wt %, 20 wt %, 30 wt %, 40 wt %, 50 wt %, 80 wt % and up to 100 wt % weight, respectively, were prepared. In these reactions, DMSO was used as the solvent and azoisobutyrylnitrile (AIBN) was used as radical initiator. Reactions proceeded under inert nitrogen atmosphere.

For the preparation of hydrogels specifically suitable for soft contact lenses, HEMA and a carbohydrate monomer were simultaneously polymerized and cross-linked with ethylene glycol dimethacrylate (EGDMA) in the presence of aqueous solution. For soft contact lenses hydrogels, carbohydrate monomer concentrations were, preferably, below 40 wt % and more preferably below 20 wt % to maintain the mechanical strength but assure the appropriate hydrophilicity and wettability. Hydrogels suitable for medical implants were prepared similarly except that the content of the carbohydrate monomer could be higher depending on the type of implant and its prospective function.

The HEMA-carbohydrate hydrogel polymers were characterized by infrared spectroscopy (FAIR). FAIR spectra of p(HEMA) and copolymers of HEMA with either 10% or 20% of carbohydrate monomer 1 showed the peaks at 1728 $cm^{-1}$ which represent the ester carbonyl (C=O) stretching band common to all of the hydrogels. Hydrogels comprising 10% or 20% of monomer 1 showed an additional peak at 1630 $cm^{-1}$ corresponding to the presence of the amide carbonyl (N—C=O) group unique to the carbohydrate acrylamide. Furthermore, the intensity of peak also correlated with the relative percentage of the carbohydrate acrylamide.

Hydrogels prepared by this method were additionally tested for their water content using the equilibrium water content (EWC) measurements, differential scanning calorimetric (DSC) measurements, and X-ray photoelectron spectroscopy (XPS) measurements.

4. Properties of Carbohydrate Hydrogel

Mechanical strength, softness, pliability, hydrophilicity, wettability and low protein binding and adsorption are primary requirements for hydrogels suitable for use as biomedical implants including the soft contact lenses. To acquire these properties, surface characterizations of the hydrogels are of primary importance. The surface properties of hydrogels are critical for determining their interactions within a physiological environment.

Several techniques including contact angle measurements, XPS, static secondary ion mass spectroscopy (SHIMS), and the thermal behavior of the copolymer measured by DSC were used for surface characterizations of the novel hydrogels of the invention.

i. Equilibrium Water Content Measurements

The equilibrium water content (EWC) is the most fundamental property of the hydrogel. Many of the properties of hydrogels, such as oxygen permeability, wettability and biocompatibility are predominantly controlled by the amount of water in the gel.

Previously, attempts have been made to develop hydrogels with high EWC. However, most of the prior hydrogels tend to bind and adsorb proteins, bacteria and lipoproteinaceous debris, a very undesirable event causing clouding of soft contact lenses and eye infections. This problem can only be eliminated by designing hydrogels having a very low protein binding and adsorption.

EWC of the new hydrogels was determined by submerging the HEMA-carbohydrate hydrogels in deionized water and observing their hydration. The detailed procedure is described in Example 13.

The EWC of the current HEMA-carbohydrate copolymers containing monomer 1, 2, 3, 4 or 5 is seen in FIG. 1. As shown in FIG. 1, EWC increased steadily with the increasing content (wt %) of carbohydrate monomers present in the hydrogel. The presence of carbohydrates in the hydrogel matrix increased the EWC of copolymers in a percentage-dependent fashion. The carbohydrates with the greatest numbers of polar hydroxyl groups (monomers 3 and 4) had the most significant impact on the EWC, increasing the value from 40% (no carbohydrate present) to 70% (20% carbohydrate by weight present). Monomers 1 and 2, compounds containing only three hydroxyl groups, while showing a similar trend, were not as potent in elevating water content as monomers 3 and 4. Within HEMA copolymers, the water retention behavior of monomer 5 containing five hydroxyl groups and a PEG group, was similar to monomer 1.

FIG. 1 shows water content of hydrated copolymers as a function of concentration (0–25 wt %) of monomers 1–5.

As seen in FIG. 1, the EWC of the p(HEMA) not containing any carbohydrate was around 40%. When any one of the sugar monomers 1–5 was added to HEMA, the water content immediately began to increase. At 10 wt % concentration of the monomers 1, 2 and 5, the EWC reached about 45%, while for monomers 3 and 4, at the same 10 wt % concentration, the EWC increased to about 55%. With increasing concentration of the monomers above 10 wt %, the water content increased more rapidly. For monomers 1 and 5 at 20 wt % concentration, the EWC increased to about 60 and 63%, respectively. Monomer 2, at 20 wt %, had EWC of about 55%. Monomers 3 and 4 when added to HEMA in 20 wt % concentration were unusually effective in increasing water content above 65%. When 20 wt % of carbohydrate monomer 3 was added to the HEMA copolymer, the EWC reached to 70%. All carbohydrate containing hydrogels showed higher water content than p(HEMA).

The results of this study shows that the introduction of a saccharide group into a hydrogel system greatly enhances the water content of the hydrogel. The higher water content, in turn, increases oxygen permeability and wettability of the hydrogel materials, making these new hydrogels particularly suitable for fabrication of medical implants and soft contact lenses.

ii. Measurement of Water Retention Abilities

In addition to the high water content of the hydrogel, it is important and necessary for the hydrogel to be able to retain the water within the hydrogel. The strength with which water is bound within the HEMA-carbohydrates hydrogel can be quantified by measuring the temperature at which water is released during heating using differential scanning calorimetry (DSC).

The technique determines the loss of water from a hydrated hydrogel as a function of temperature and a constant rate of heating as an irreversible transition which gives a broad DSC peak. The temperature corresponding to the peak maximum is taken as a qualitative measure of the water retention ability of a given polymer. Higher peak-maximum temperatures reflect greater water retention. Results of DSC measurements are shown in FIG. 2.

Figure 2:
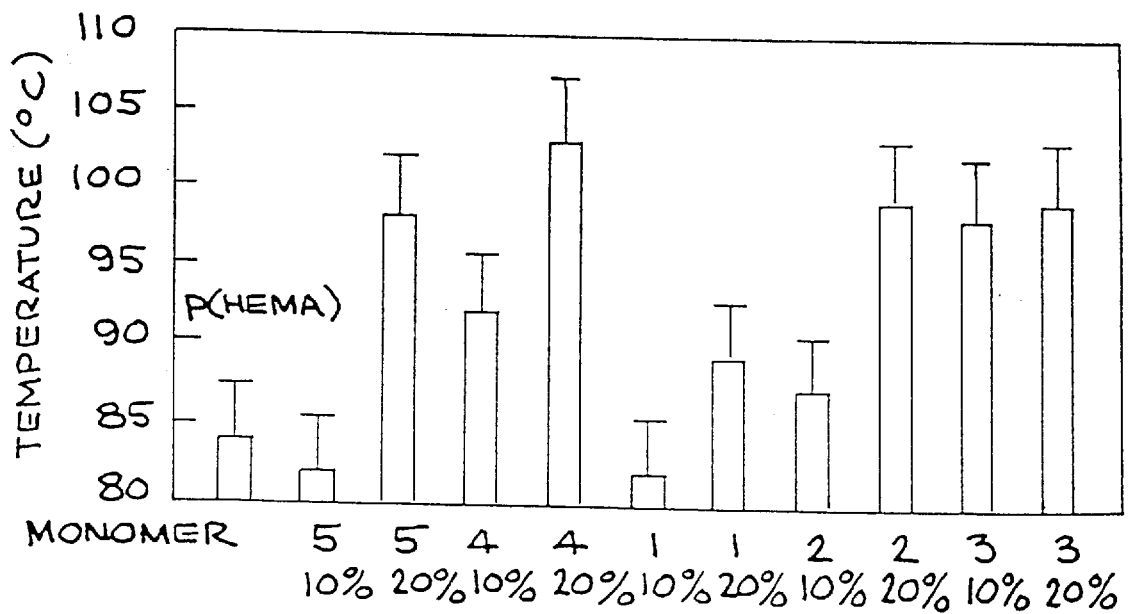
FIG. 2 shows a differential scanning calorimetry (DSC) peak maximum temperatures of hydrated HEMA-carbohydrate hydrogel copolymers containing 10 wt % or 20 wt % of carbohydrate monomer 1, 2, 3, 4 or 5.

FIG. 2 shows the DSC peak-maximum temperatures for the HEMA hydrogel copolymers containing different concentrations of monomers 1–5.

As seen in FIG. 2, the presence of carbohydrate moieties in the hydrogel increases the water retention ability of HEMA-carbohydrate hydrogels, and the magnitude of the increase is dependent on the percentage of the carbohydrate. For example, the monomer 4, at 20 wt %, reached the temperature at the peak-maximum of over 100° C. Monomers 2, 3 and 5, all at 20 wt %, also show good water retention ability having the peak-maximum temperature slightly lower than 100° C. Monomers 3 and 4 show the good water retention ability even at 10 wt % concentration. All but compounds 5 and 1, at 10 wt % concentration, show the higher peak-maximum temperature and therefor have a better water retention ability than p(HEMA).

iii. Contact Angle Measurement

Materials with both high hydrophilicity and high surface wettability are fundamental for biomedical implant applications as they are less prone to structural rearrangements upon exposure to aqueous fluids. High hydrophilicity and wettability of the hydrogels are essential for interfacing with blood and living tissues because they determine and affect adhesion, binding and adsorption of the biological materials, such as protein, lipoproteins, bacteria, etc., to or on the hydrogels. From this point of view, a low adsorption of proteins is very important aspect of biocompatibility of the hydrogel.

Surface hydrophilicity or wettability of a solid material can be readily estimated by contact angle measurement using a liquid of known polarity. The contact angle of a liquid of known polarity on a solid surface serves a quantitative indicator of surface wettability. The detailed procedure for contact angle measurements is described in Example 14.

Contact angle measurements of the hydrogels of the invention were performed on the film surface of the new hydrogels. To measure contact angles of the novel hydrogels copolymers containing monomers 1–5, solvents with different polarities, namely methylene diiodide which is hydrophobic and glycerol, which is hydrophilic, were used. The two selected solvents form stable droplets on hydrophilic materials with no noticeable penetration or swelling.

Figure 3:
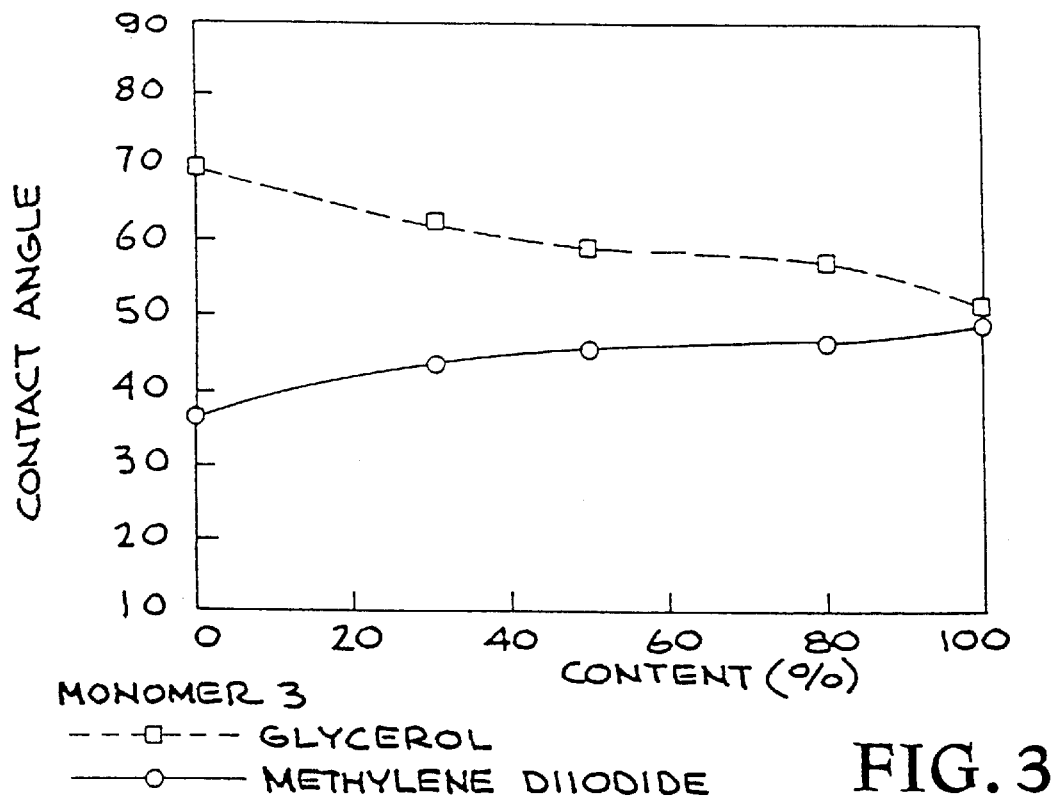
FIG. 3 shows effect of content of carbohydrate monomer 1 on the contact angles of glycerol (-□-) and methylene diiodide (-○-) on the surface of HEMA copolymer films containing monomer 1.
Figure 4:
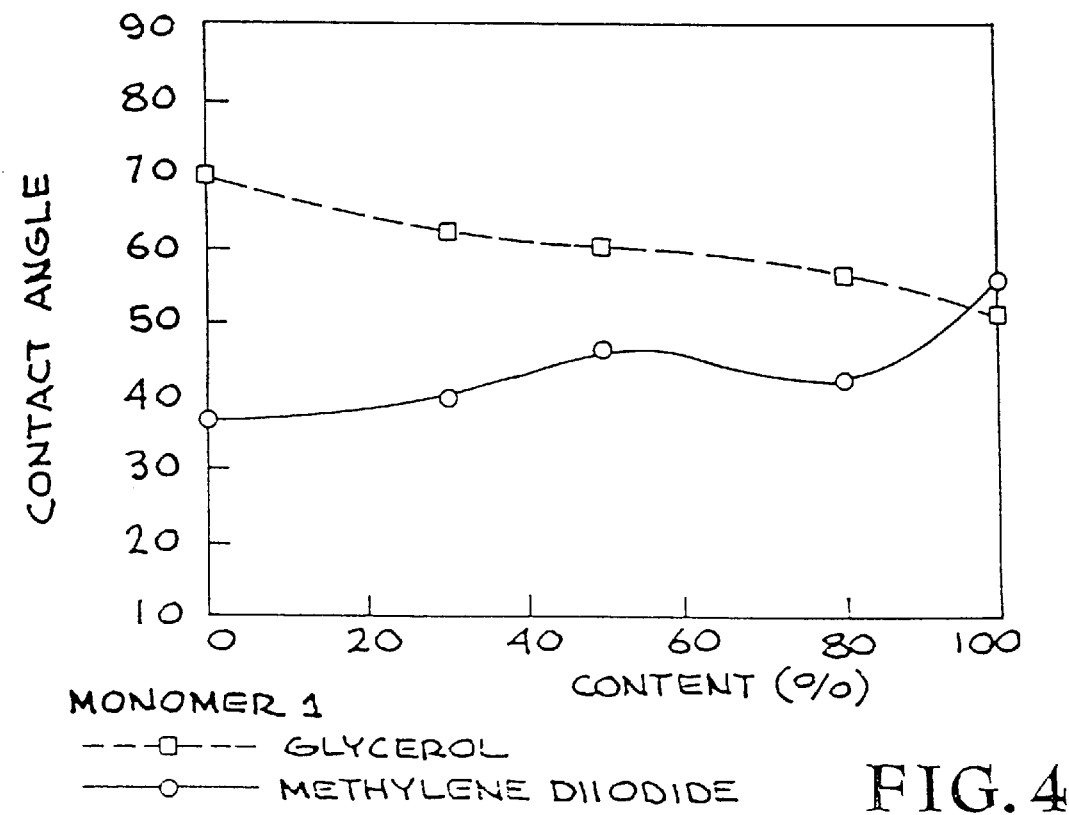
FIG. 4 shows the effect of content of carbohydrate monomer 3 on the contact angles of glycerol (-□-) and methylene diiodide (-O-) on the surface of HEMA copolymer films containing monomer 3.

Results of contact angle measurements are seen in FIGS. 3 and 4 which show the correlations between the monomer's content (wt %) and contact angles of monomers 1 and 3. Compound 3 is an open chain saccharide derivative containing five hydroxyl groups and therefore is considered to be most hydrophilic among all the prepared monomers. Monomer 1 is the derivative of rhamnose containing three hydroxy groups and is therefore considered to be less hydrophilic. Monomers 1 and 3 were incorporated into HEMA in concentrations from 0 wt % to 100 wt % and the contact angles of methylene diiodide and glycerol placed on the copolymer film surface were measured.

FIG. 3 shows the effect of increased percentage per weight of HEMA-monomer 3, and FIG. 4 shows the effect of increased percentage per weight of HEMA-monomer 1 on contact angles.

As seen in FIGS. 3 and 4, with the increased percentage of the monomers, the contact angles of methylene diiodide increased and that of glycerol decreased gradually for both hydrogels. The observed increase of contact angle of methylene diiodide indicated that with the gradually increased incorporation of carbohydrate content into HEMA, the hydrophilicity of both these copolymers increase gradually. Likewise, the contact angles of glycerol decreased with the increasing content of the monomer within the hydrogel, showing that the hydrophobicity of the copolymers decreased with the increasing content of the carbohydrate monomer. As expected, the more hydrophilic monomer 3 had the bigger impact on the copolymer hydrophilicity showing the highest contact angle with methylene diiodide and the lowest angle with glycerol. Monomer 1 which is much less hydrophilic has a lesser impact on the copolymer hydrophilicity and the lower contact angle, as seen in FIG. 4.

iv. X-Ray Photoelectron Spectroscopy

X-ray photoelectron spectroscopy (XPS) provides information such as elemental compositions and chemical bonding at the surfaces of polymer samples. XPS has been applied extensively to the surface characterization and analysis of hydrogels, both in dry and hydrated state. XPS survey spectrum provides qualitative information on the elements which are present at the surface of copolymers. XPS analysis utilized to determine the surface composition of HEMA-carbohydrates 1–5 at dehydrated state detected the presence of nitrogen and/or sulfur in the XPS spectrum as an indicator for the presence of carbohydrate moiety at the surfaces of polymers. Results are seen in FIG. 5.

Figure 5:
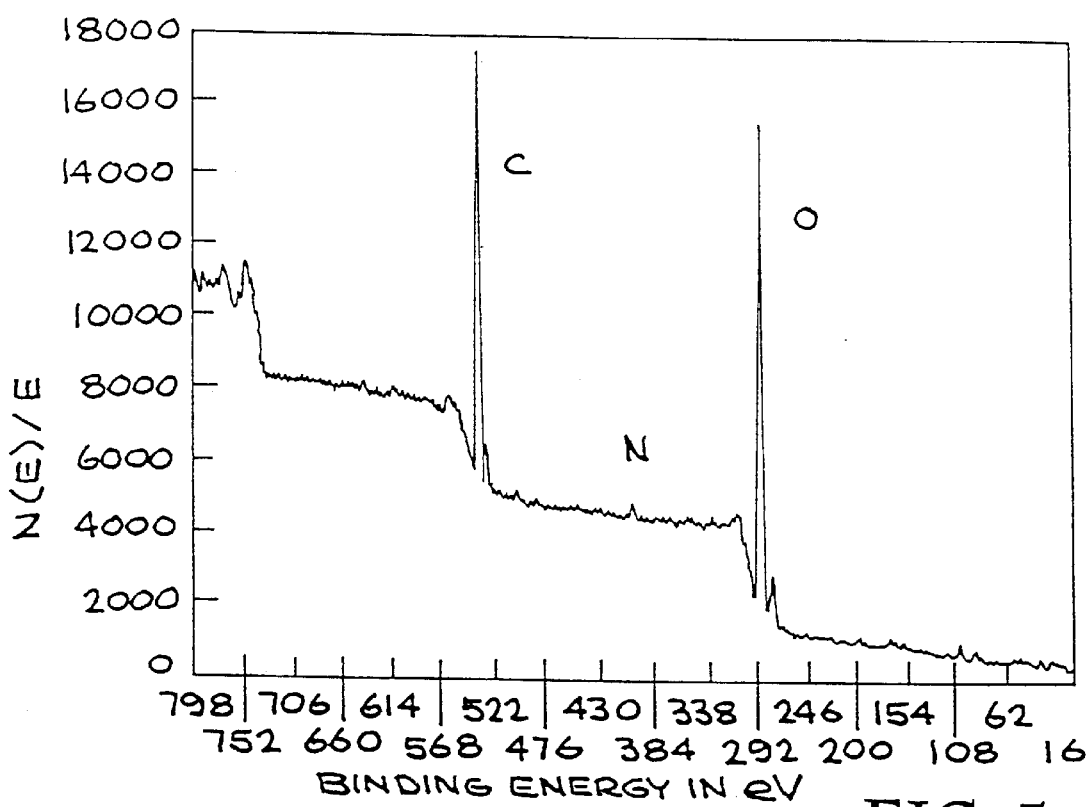
FIG. 5 shows X-ray photoelectron spectroscopy (XPS) survey spectrum of a HEMA-carbohydrate hydrogel composed of 10 wt % of monomer 1.

FIG. 5 shows a typical survey spectrum of a HEMA-carbohydrate hydrogel. Specifically, FIG. 5 represents XPS survey spectrum of HEMA-monomer 1 (10 wt %); other monomers showed similar results. As expected, C, O and N were detected from all the hydrogel copolymers containing monomers 1–5. In addition, S was recorded in HEMA hydrogel containing monomer 2. Control samples of p(HEMA) without the carbohydrate moiety contained neither nitrogen nor sulfur.

The atomic concentrations of C, O, N and S of all the monomers used for the preparation of copolymers were calculated. For sugar monomers 1, 2 and 5, the ratio of carbon/oxygen was higher than for HEMA; for sugar monomers 3 and 4, the ratio of carbon/oxygen was lower than for HEMA. Table 1 summarized detailed multiplex spectra of chemical elemental composition of HEMA-hydrogels containing monomers 1 and 3. As seen in Table 1, regardless of the theoretical atomic concentrations of C, O and N, XPS spectra of both hydrogels showed much higher concentration of carbon and lower concentration of oxygen and nitrogen.

TABLE 1

| Monomers | HEMA calc.data | HEMA XPS.data | 1 calc.data | 1 XPSdata | 3 calc.data | 3 XPS.data |
|---|---|---|---|---|---|---|
| C % | 66.7 | 73.4 ± 0.4 | 62.5 | 72.0 ± 2.0 | 56.3 | 72.8 ± 0.4 |
| O % | 33.3 | 26.5 ± 0.4 | 31.3 | 24.5 ± 1.0 | 37.5 | 23.5 ± 0.2 |
| N % |  |  | 6.3 | 3.4 ± 0.4 | 6.3 | 3.7 ± 0.3 |

Table 2 shows XPS elemental compositions of HEMA-carbohydrate hydrogels. In Table 2, the obtained XPS compositions of C, O, N and S of HEMA-carbohydrate hydrogels containing 10 wt % or 20 wt % of monomers 1–5 are compared to their theoretical atomic concentrations. For this purpose, the theoretical atomic concentrations of elements were calculated based on the bulk structures of the copolymers. The actual atomic concentrations of nitrogen and/or sulfur, detected in all measured hydrogels, were higher than the expected theoretical data. For example, in the hydrogel containing 20 wt % of monomer 2, N % and S % were nearly two times higher than the stoichiometric calculated bulk composition.

TABLE 2

|   | 1 10% | 1 20% | 2 10% | 2 20% | 3 10% | 3 20% | 4 10% | 4 20% | 5 10% | 5 20% |
|---|---|---|---|---|---|---|---|---|---|---|
| C | 66.3 | 65.8 | 66.3 | 65.8 | 65.6 | 64.6 | 65.9 | 65.1 | 66.8 | 66.9 |
| O | 33.1 | 32.9 | 32.5 | 31.8 | 33.7 | 34.2 | 33.5 | 33.7 | 32.9 | 32.5 |
| N | 0.6 | 1.2 | 0.8 | 1.6 | 0.6 | 1.2 | 0.6 | 1.2 | 0.3 | 0.6 |
| S |  |  | 0.4 | 0.8 |  |  |  |  |  |  |
| C | 80.1 | 74.6 | 68.5 | 67.1 | 72.6 | 74.3 | 76.2 | 73.8 | 78.8 | 78.2 |
| O | 18.9 | 23.9 | 29.3 | 29.0 | 26.4 | 24.4 | 22.4 | 24.3 | 20.1 | 20.9 |
| N | 1.1 | 1.6 | 1.5 | 2.7 | 1.1 | 1.4 | 1.5 | 1.9 | 1.2 | 1.3 |
| S |  |  | 0.7 | 1.2 |  |  |  |  |  |  |

The upper half of the Table 2 shows theoretical atomic concentrations (wt %); the lower half of the Table 2 shows obtained concentrations (wt %).

Figure 6A:
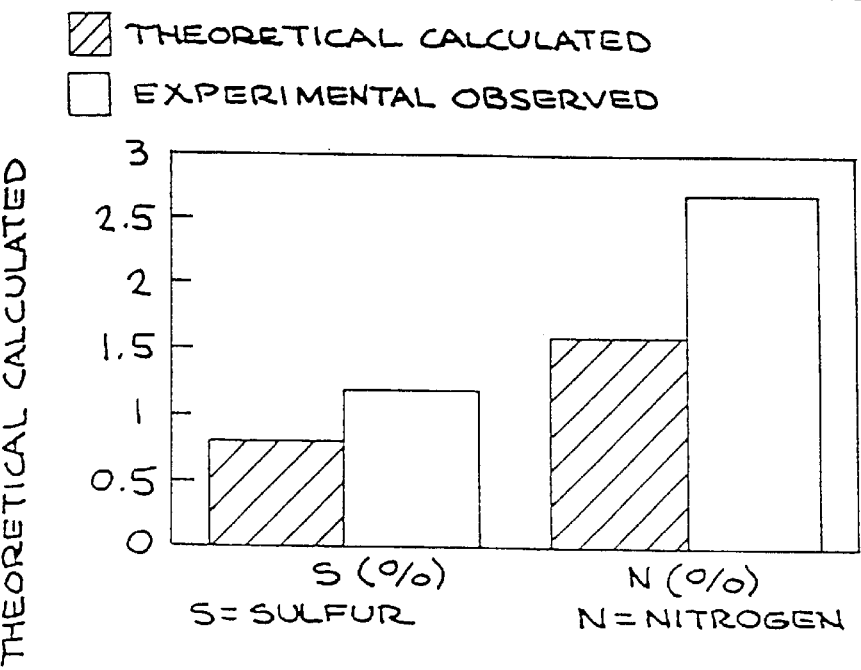
FIG. 6 shows elemental nitrogen, sulfur, carbon and oxygen composition of a HEMA-carbohydrate copolymer composed of 20 wt % of monomer 2 by XPS analysis. Calculated values are compared with experimentally observed values.
Figure 6B:
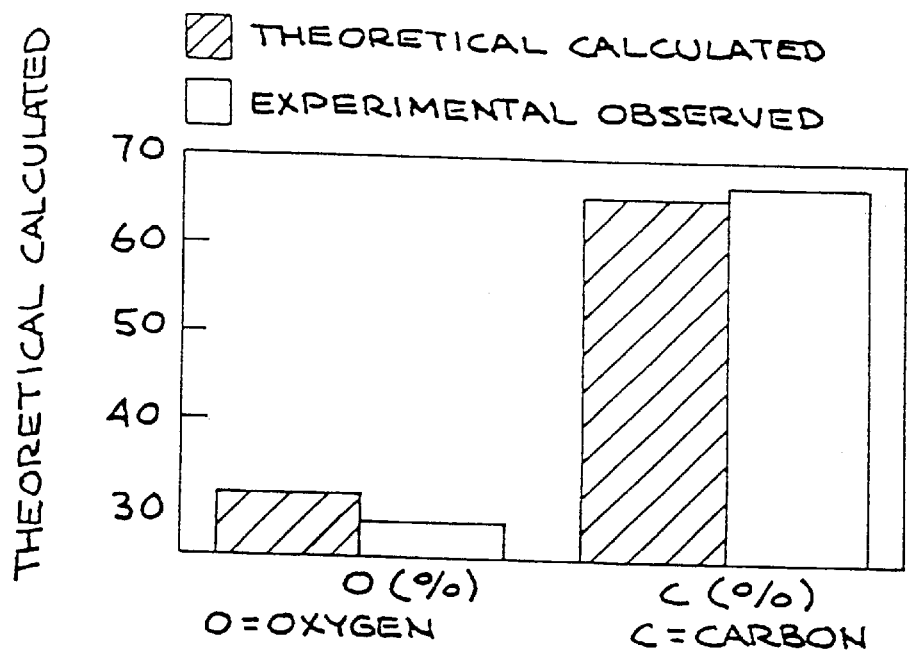

Results of these studies are shown in FIG. 6 which compares theoretical calculated data with actual observed data of XPS elemental compositions of HEMA-monomer 2 (20 wt %). FIG. 6A shows theoretical and actual values of sulfur and nitrogen; FIG. 6B shows theoretical and actual values of oxygen and carbon.

Elemental composition determined by XPS and the angular dependent XPS data together confirm that in HEMA-carbohydrate copolymers, carbohydrate moieties are localized on the surface of the polymers. This data indicate that hydrophobic non-polar atoms such as carbon-carbon polymer chains are localized at the surface of the samples and hydrophilic groups (mostly hydroxyl group and spacers) face towards the bulk of the polymers. Stopped here.

V. Hydrophilicity of the HEMA-Carbohydrate Hydrogels

Water present in the hydrogel acts as a medium of transport for dissolved oxygen and small molecules, and also as a bridge between the hydrogel synthetic materials and body fluids. Thus, the water binding properties of hydrogel materials are crucial for their function within a bioenvironment.

For example, the eye acquires oxygen directly from the atmosphere and contact lenses placed on the surface of the eye in general compromise this oxygen supply. When the soft contact lenses are used, only the oxygen dissolved in the water of the hydrogel matrix is provided to the cornea. Therefore, the oxygen permeability of a hydrogel material is directly related to the equilibrium water content and the higher is the EWC, the better is the oxygen permeability.

In designing improved hydrogel materials for contact lenses or biomedical implant applications, enhanced water content and lowered protein adsorption on surfaces are the two very important features for successful design. The novel hydrogel materials can be made more hydrophilic by increasing the number of polar functional groups, resulting in a higher degree of hydration, and in increased equilibrium water content and vice versa, lower number of such groups results in lesser hydration and decreased EWC.

Bulk copolymerization of HEMA and carbohydrate-acrylamide monomers 1–5 in the presence of 2 wt % ethyleneglycol dimethacrylate (EGDMA) as a cross-linker furnished hydrophilic hydrogels with enhanced equilibrium water content values. Based on the structural features of monomers 1–5, the hydrophilicity of the gels increases linearly with increasing amounts of polar components, namely the carbohydrate monomers containing the amide functionality or multiple hydroxyl groups. Results are seen in FIG. 7.

Figure 7:
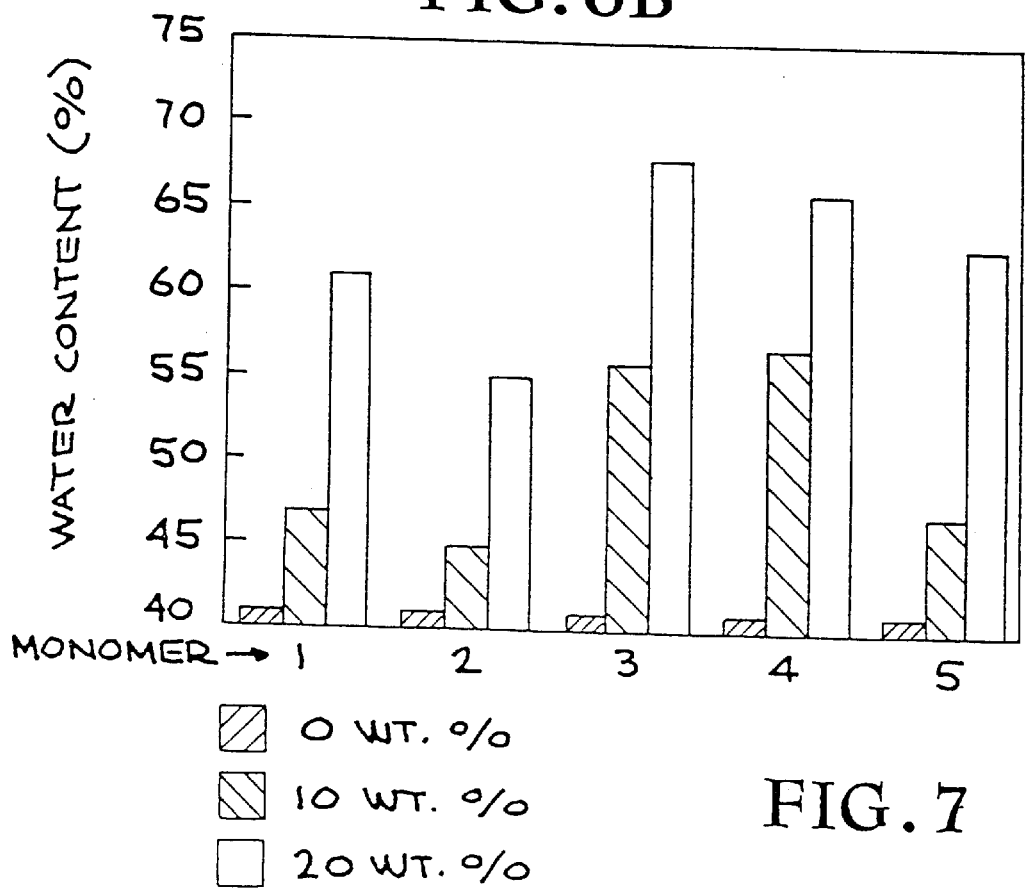
FIG. 7 shows equilibrium water content (EWC) of the HEMA-carbohydrate hydrogels as a function of the amount wt % of carbohydrate monomers 1–5.

As seen in FIG. 7, monomers 1 and 2, having the least number of hydroxyl groups, provide a moderate increase in the water content when present in 10 wt %. Monomers 3–5, by contrast, increase the water content of the HEMA hydrogels to about 55% at 10 wt % to over 65% when present at 20 wt % incorporation level. At 20 wt % concentration, the monomer 5-HEMA hydrogel increases the water content to levels observed for monomers 3 or 4 HEMA hydrogels.

Studies and data obtained with the novel hydrogels of the invention show that the hydrogels of the invention have increased equilibrium water content, increased bulk water retention, increased hydrophilicity, wettability and decreased protein binding activity compared to p(HEMA) used previously for fabrication of contact lenses and biomedical implants.

Hydrogels for biomedical implants including soft contact lenses are prepared by correlating the monomer structural features, hydrogel physical characteristics and protein adsorption behavior. These characteristics and their correlations are then used in designing carbohydrate-based hydrogels specifically suitable for their intended biomedical applications, such as for bone or cartilage implants, breast implants, cosmetic uses, etc.

B. Biological Testing and Properties

The hydrogels comprising copolymerized HEMA with the carbohydrate moiety have various biologically active functionalities important for their biocompatibility. Two of these properties are the low intrinsic protein binding and protein absorption. Protein adsorption on hydrogel surfaces is dependent on a variety of factors such as the chemical nature of the surface including hydrophilicity, hydrophobicity and charge density, and also on the size and chemical composition of the exposed proteins.

Since different biological media are composed of rather different types of proteins, the materials designed for specific implant applications must be, and were, tested using those proteins most likely encountered in vivo. Consequently, the tests were performed on the hydrogels tested for their suitability as materials for soft contact lenses.

1. Contact Lenses Hydrogels

In the context of soft contact lenses increasing the water content of a hydrogel material up to a point where its tensile strength is not compromised increases comfort of the eye, and enhances the transport of oxygen to the cornea and to the epithelial layer.

The currently commercially available hydrogel-based contact lenses have been classified by the Food and Drug Administration (FDA) into four groups. Group 1: low water content-nonionic; Group 2: high water content-nonionic; Group 3: low water content-ionic; Group 4: high water content-ionic. Both in vivo and in vitro studies indicate a high deposition of protein lysozyme on Group 4 hydrogel lenses, and it is believed that this protein, due to its small size, is absorbed into the hydrogel matrix (*Biomaterials*, 16:685 (1995).

Many of the currently available soft contact lenses have undesirable interactions between the proteins and the hydrogels of the contact lenses. Both in vivo and in vitro studies indicate a high deposition of protein lysozyme on Group 4 hydrogel lenses, and it is believed that this protein, due to its small size, is absorbed into the hydrogel matrix (*Biomaterials*, 16:685 (1995). This leads to the poor toleration of these lenses and raises concerns about safety of their extended wear.

Biocompatible hydrogel materials of the invention were specifically engineered for extended wear soft contact lens applications. For this purpose, new hydrogel systems based on 2-hydroxyethyl methacrylate (HEMA) and five structurally different carbohydrate acrylamide monomers present in different concentration were constructed and tested for in vitro protein and lipid adsorption using an artificial tear fluid (ATF) containing mixtures of proteins and lipids that are commonly found in human tear fluid and in contact lens deposits. Major components of both tear proteins and contact lens deposits are lysozyme, albumin, mucin, lactoferrin, IgA and IgG.

The carbohydrate constituents of the current hydrogel were found to increase the equilibrium water contents of p(HEMA) hydrogels up to as high as 70 wt % at an incorporation level of 20 wt %. But, unlike the conventional water enhancing additives like methacrylic acid or N-vinyl pyrrolidine, the carbohydrate monomers did not adversely affect in vitro protein adsorption. In fact, with two of the monomers, compounds 3 and 4 incorporated in HEMA, the protein adsorption from artificial tear fluid (ATF) was reduced to about 50 wt % of that observed for pure p(HEMA) hydrogels.

Because of their increased hydrophilicity, wettability and low protein binding and adhesion, novel hydrogels of the invention are especially useful as materials for biomedical implants and particularly for soft contact lenses.

2. In Vitro Protein Adsorption and Binding

For studies of in vitro protein absorption, ATF solution using a protocol described in Example 17 was used. The preparation contained three of the major proteins found in tears and lens deposits, namely, lysozyme, albumin and mucin, with a total protein concentration of 3.2 mg/mL, as well as all recommended lipid components.

Hydrogels (1×1 $cm^2$ size pieces) prepared from p(HEMA) and HEMA-carbohydrate containing 10 wt % or 20 wt % of each of the carbohydrate monomers were incubated in ATF for various time periods at 37° C. The adsorbed proteins were quantified using the BCA assay, as described in *Macromol. Chem. Phys.*, 195:1953 (1994).

The results of the study are presented in FIGS. 8A–E. In each figure, protein adsorption behavior of poly(HEMA) is plotted along with that of carbohydrate-HEMA hydrogels containing monomers 1–5.

As seen in FIGS. 8A–8E, for all the hydrogels in the present study, the majority of the protein adsorption occurred within the initial four hours, and further incubation of hydrogels in ATF for longer periods did not significantly increase their adsorption. In some cases, there was a clear reduction of adsorbed proteins at incubation periods of 24 hours and 72 hours.

Figure 8A:
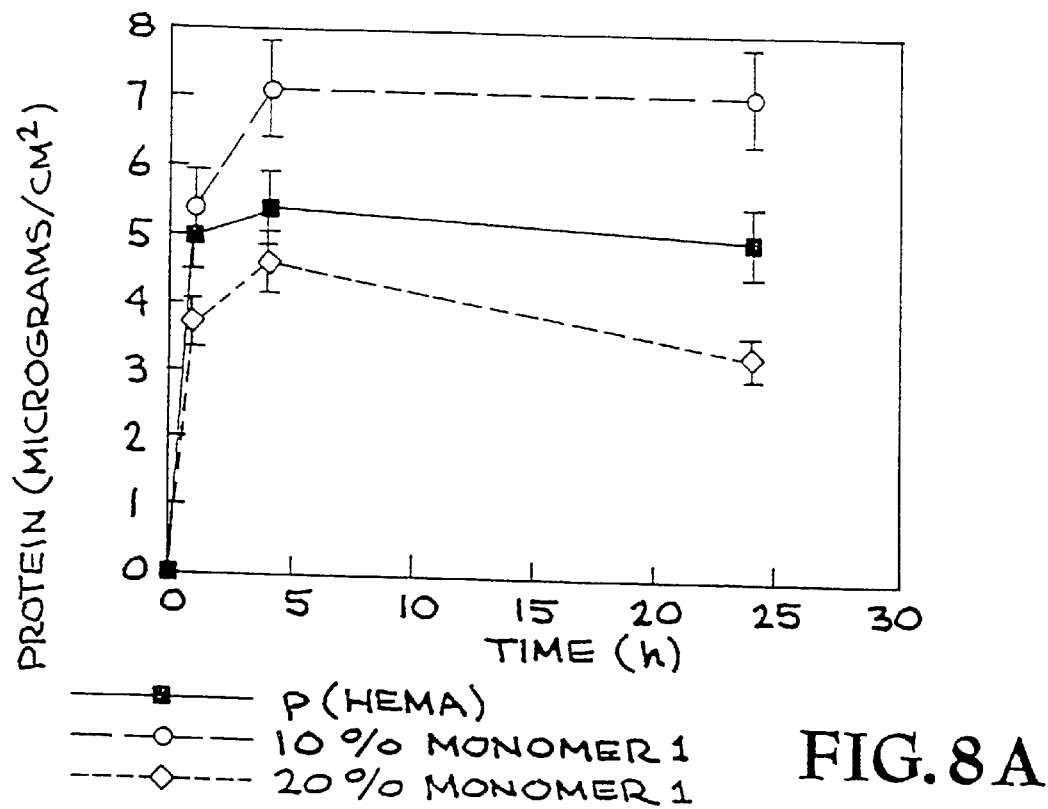
FIG. 8 shows the amount of protein (micrograms/cm$^2$) adsorbed on HEMA and on HEMA-carbohydrate hydrogels containing monomer 1 (FIG. 8A), 2 (FIG. 8B), 3 (FIG. 8C), 4 (FIG. 8D), and 5 (FIG. 8E) as a function of incubation time (hours) in artificial tear fluid (ATF) at 36° C.
Figure 8B:
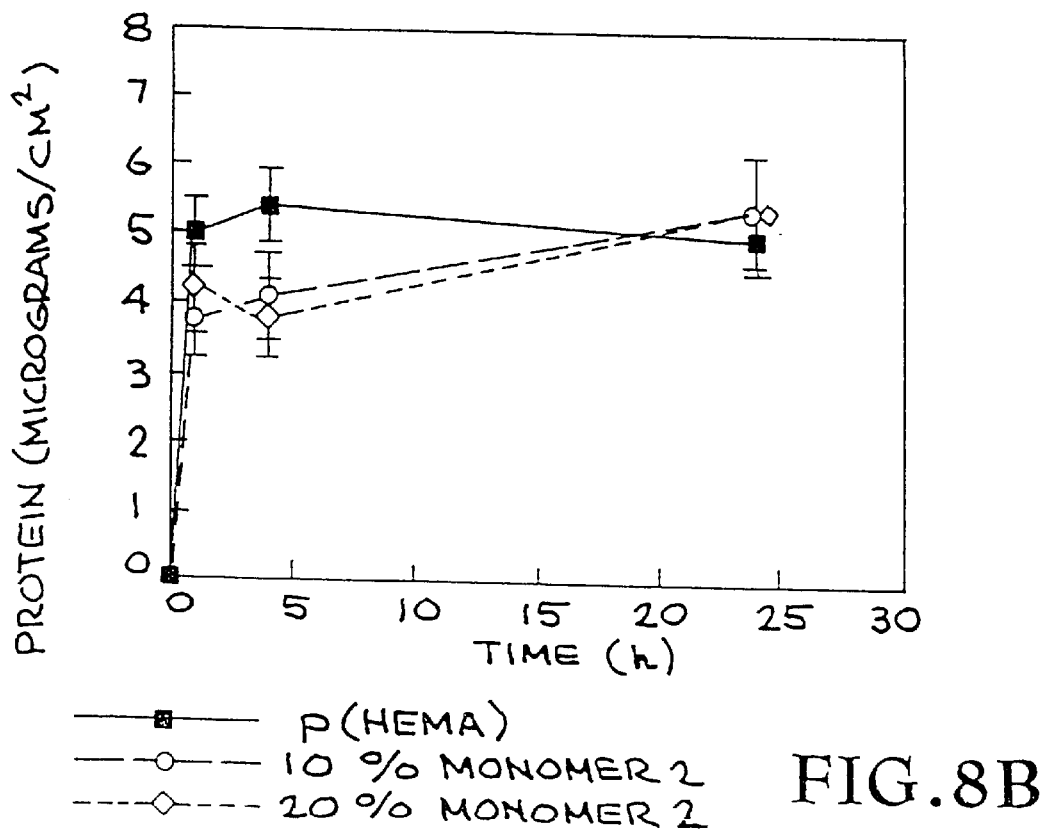
Figure 8C:
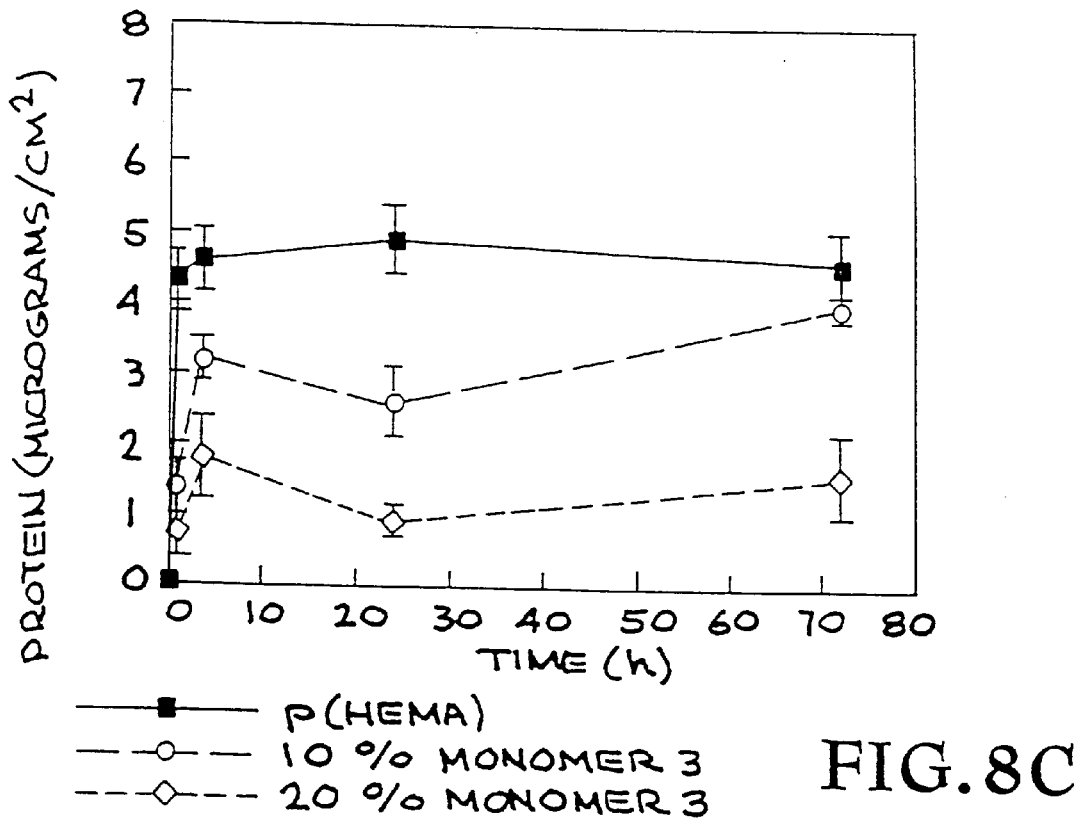
Figure 8D:
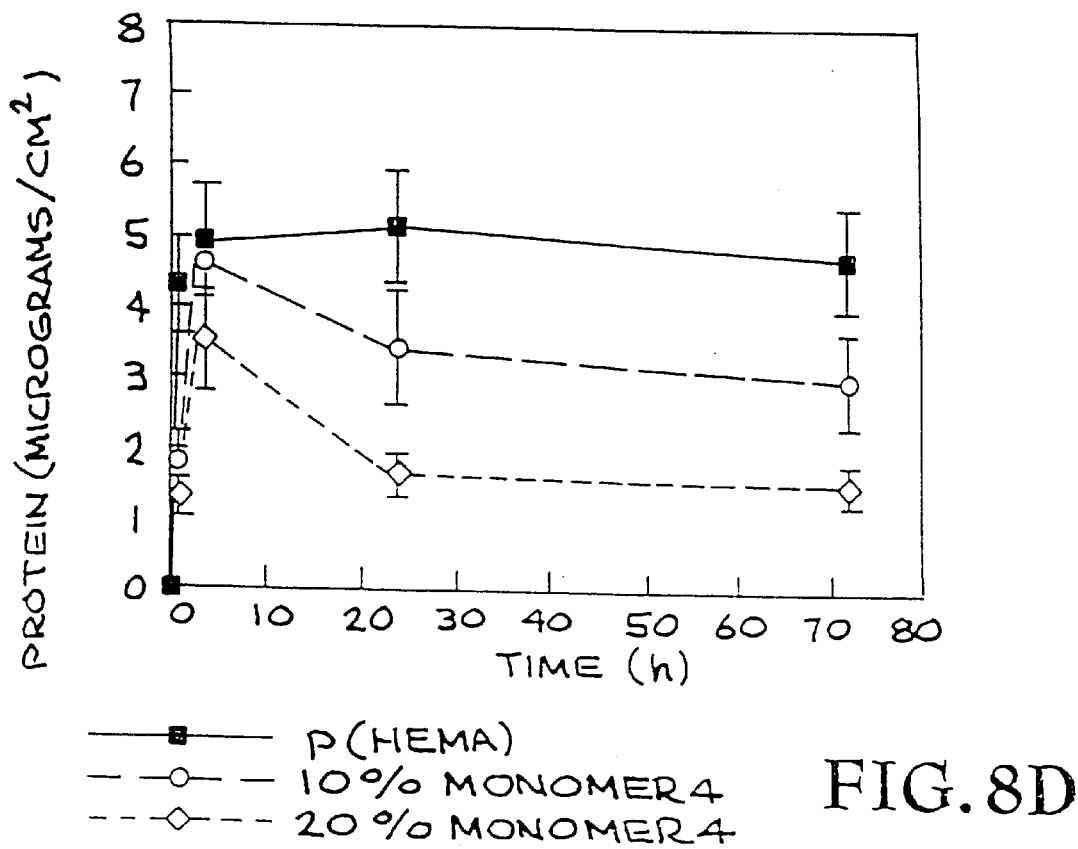
Figure 8E:
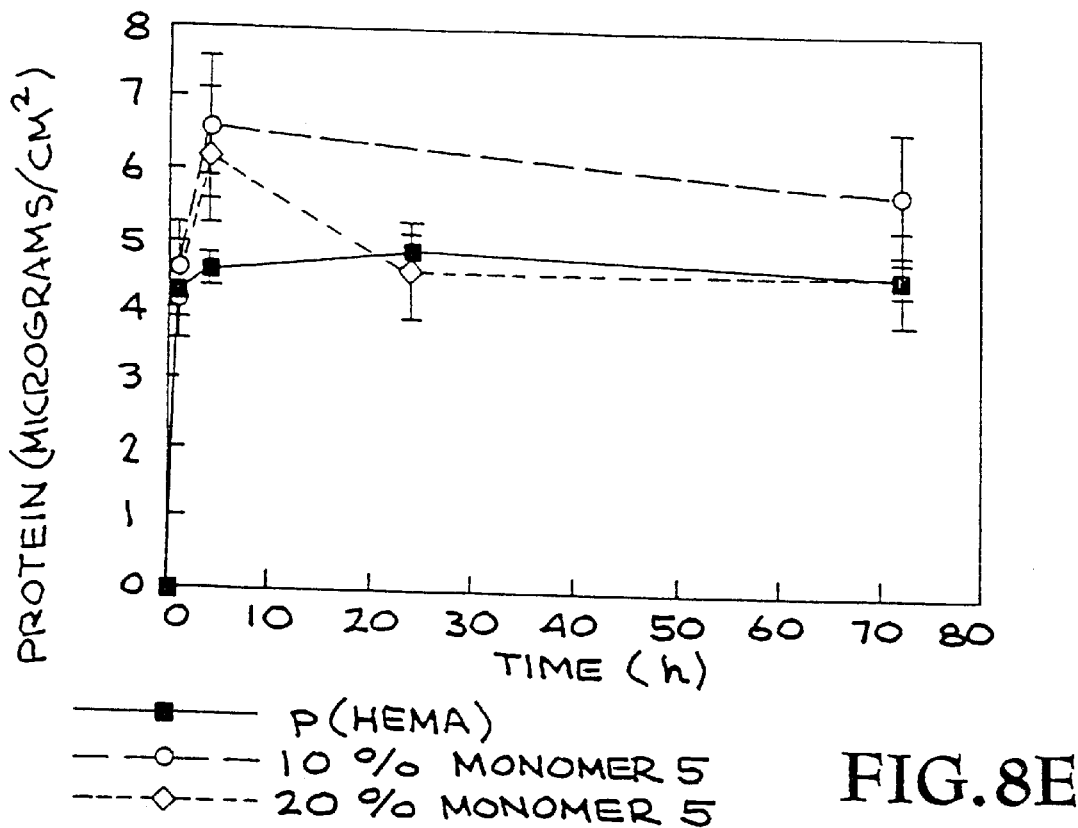

The results in FIGS. 8A–E show the effect of HEMA-carbohydrate and p(HEMA) hydrogels on the protein adsorption. Most importantly, the results seen in FIGS. 8A–F show that the incorporation of carbohydrate monomers compounds 1–5 into HEMA hydrogels, while increasing the equilibrium water content, does not lead to an adversely large increase in protein binding. In fact, with increasing amounts of compounds 3 and 4 in HEMA, the protein adsorption from ATF actually decreases to levels lower than 50% of those levels observed for p(HEMA), as seen in FIGS. 8C and 8D. As seen in FIGS. 8A, 8B and 8E, HEMA-carbohydrates containing monomers 1, 2 or 5 exhibit protein adsorption behavior that depends on their concentration and is similar to p(HEMA) hydrogels, or in many cases lower than that of p(HEMA).

Figure 8F:
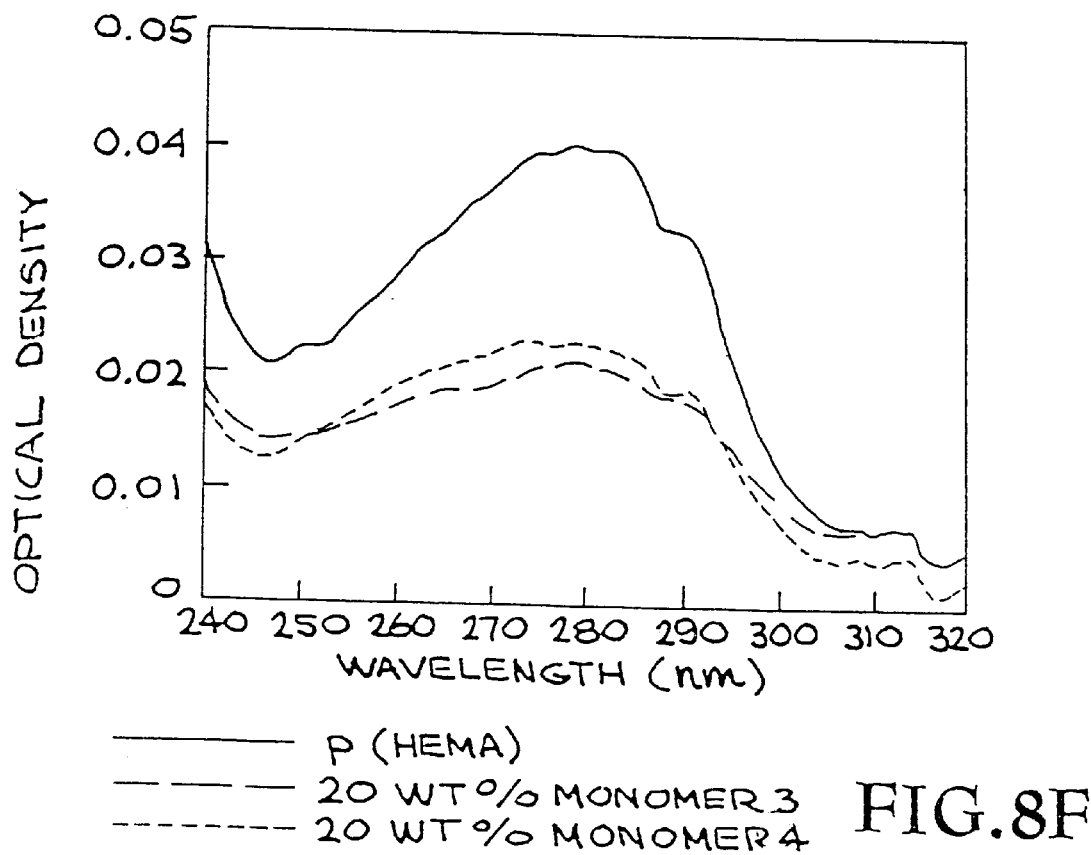

The in vitro protein adsorption behavior of carbohydrate-HEMA hydrogels shown in FIGS. 8A–E was confirmed to be reproducible in multiple sets of experiments by BCA protein analysis technique, and by measuring the UV-absorption spectra of the proteins extracted from hydrogel surfaces into surfactant solutions. FIG. 8F shows the optical densities of extracted proteins from p(HEMA) and HEMA-carbohydrate containing 20 wt % of monomers 3 or 4 which display a close correspondence to the trends observed in FIGS. 8C and 8D.

The factors that are responsible for the observed differences in protein adsorption of carbohydrate-HEMA hydrogels, such as water content, surface functionality and wettability are crucial in determining the material's resistance to protein deposition. Among the tested hydrogels, the lowest protein adsorption was observed for those hydrogels having the highest equilibrium water contents (around 66–68 wt %), namely for HEMA-carbohydrates containing 20 wt % of compounds 3 and 4 (FIGS. 7, 8C and 8D). Correspondingly, HEMA-carbohydrate hydrogels containing monomers 1 and 2 at 10 wt % having a lower water content exhibited protein adsorption that is slightly higher than or equal to that of p(HEMA) hydrogels. In contrast, HEMA-carbohydrate monomer 5 hydrogel at 20 wt %, showing comparable water content to that of monomer 3 and 4 containing hydrogels, have protein adsorption levels similar to those of monomers 1 and 2. This indicates that protein adsorption on non-ionic HEMA-carbohydrate hydrogels is not a simple function of equilibrium water content (a bulk property), but depends on a variety of factors including surface wettability and hydrophilic-hydrophobic interactions between functional groups of the proteins and polymers.

The observed protein adsorption of the hydrogels in this study reflects the differential binding affinities of different proteins from the ATF to individual hydrogel surfaces. To study the adsorption profiles of the different proteins on carbohydrate-HEMA hydrogels in more detail, the deposition of individual proteins on HEMA-hydrogels containing 20 wt % of monomers 3, 4 or 5 was determined.

Protein adsorption behavior of p(HEMA) and HEMA-carbohydrate hydrogels 3, 4, and 5 (20 wt %) was studied in a single protein solution, containing either lysozyme, albumin or mucin. The results are presented in FIG. 9.

Figure 9:
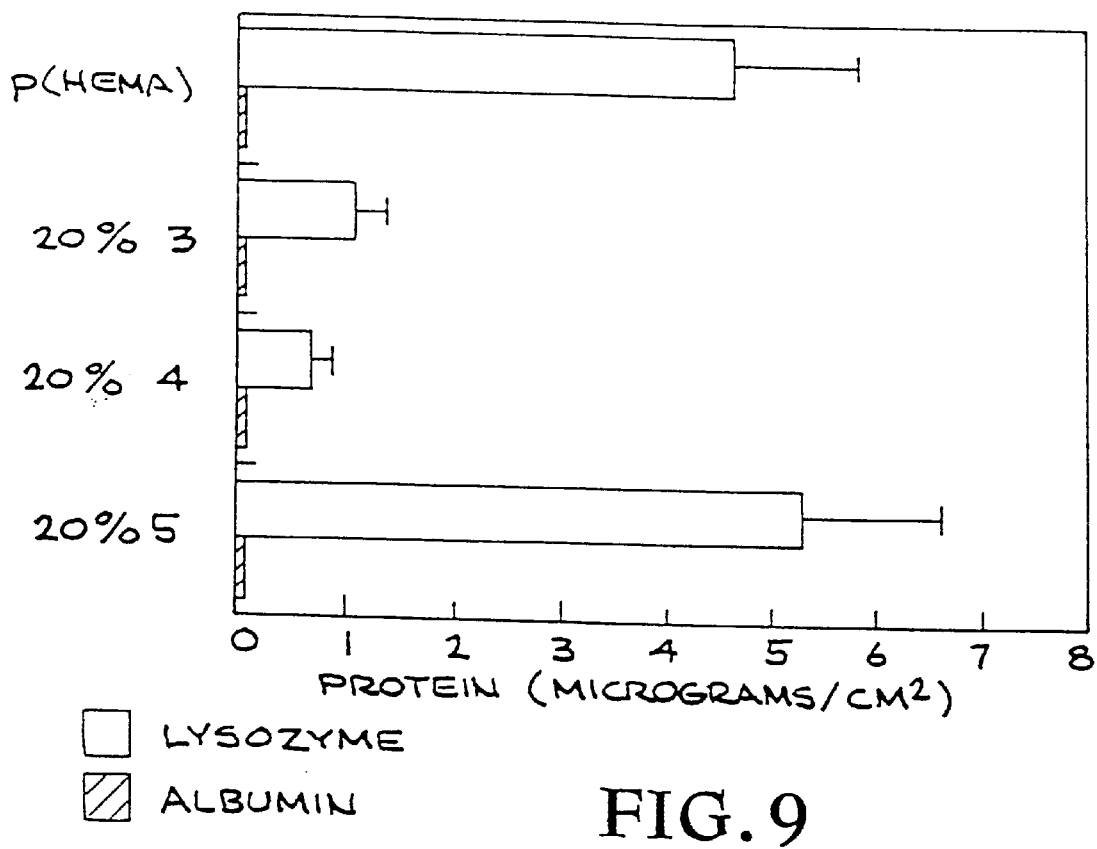
FIG. 9 illustrates adsorption of albumin and lysozyme (micrograms/cm$^2$) on HEMA-carbohydrate hydrogels containing 20 wt % of monomer 3, 4, or 5 after 24 hours incubation at 36° C.

As seen in FIG. 9, when incubated in a solution of albumin (3.2 mg/mL) for 24 hours, all four tested hydrogels exhibited negligible protein adsorption. By contrast, when incubated in lysozyme solution (3.2 mg/mL), the protein adsorption on these hydrogels was found to be almost identical to that observed in the mixture of three proteins, as seen by comparing FIGS. 9 and 8C–E.

The results of FIG. 9 provide an insight into the nature of carbohydrate-HEMA hydrogel surfaces. The very low adsorption of albumin on hydrogels of HEMA-carbohydrate containing 20 wt % of monomer 3, 4 or 5 indicates that the polymer surfaces of these hydrogels are rather polar or hydrophilic. Results seen in FIG. 9 further show that incorporation of 20 wt % of carbohydrate monomers compounds 3 or 4 into HEMA reduces adsorption of lysozyme by more than 50 wt %. Such reduction in lysozyme adsorption is a significant improvement of the material for soft contact lenses applications, as this protein has been found in high concentration both in human tears and on lens deposits and shown to increase the risk of bacterial adhesion to soft contact lenses.

The current carbohydrate-HEMA hydrogels belong to the high water content-nonionic (Group 2) class of materials. Consequently, in vitro protein adsorption behavior of the new HEMA hydrogels containing 20 wt % of monomers 3 and 4 was compared to commercial high water content-ionic (FDA Group 4) and high water content-nonionic (FDA Group 2) soft contact lenses materials. Commercial contact lenses used in the comparative studies are listed in Table 3.

Figure 10A:
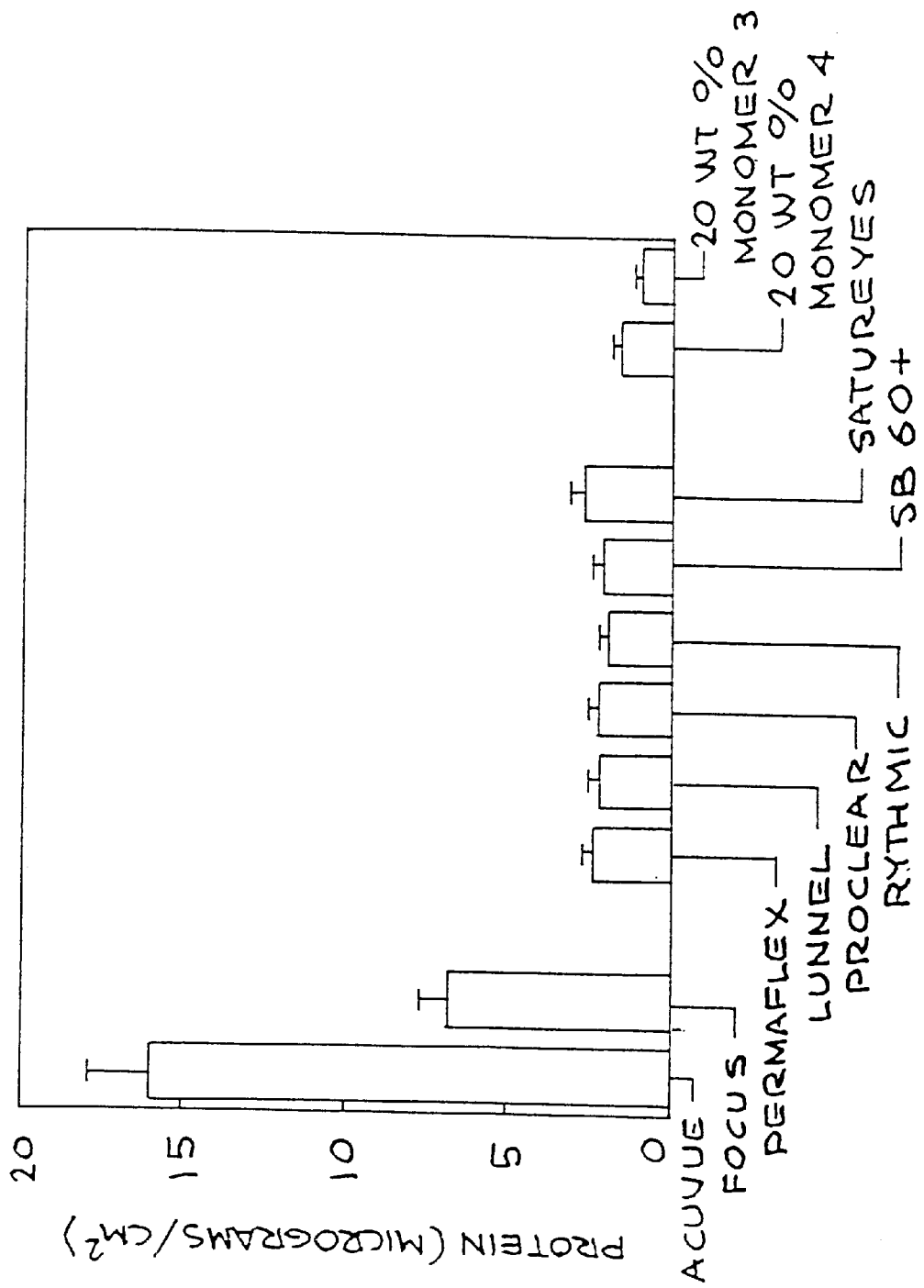
FIG. 10A (micrograms/cm$^2$)

The results of this study are presented in FIG. 10. For commercial lenses, the expected or known trends in protein adsorption based on the type of the lens material were listed. As seen in FIG. 10A, ACUVUE, and FOCUS lenses of Group 4 showed high levels of protein adsorption; PERMAFLEX, LUNNELLE, PROCLEAR, RYTHMIC, SB 60+ and SATUREYES (FDA Group 2) lenses have considerably lower levels of protein adsorption than the ionic lenses and HEMA-carbohydrate hydrogels containing 20 wt % of monomers 3 and 4 had the lowest levels of adsorption of all the tested lenses.

TABLE 3

| Lens | Company | FDA Group[a] | Composition |
|---|---|---|---|
| ACUVUE ® | Vistakon | 4 | 42% Etafilcon 58% Water |
| FOCUS ® | Ciba Vision | 4 | 45% Vifilcon 55% Water |
| PERMAFLEX ® | Barnes Hind | 2 | 26% Surfilcon A 74% Water |
| LUNNELLE ® | Essilor | 2 | 30% MMA-NVP 70% Water |
| PROCLEAR ® | Biocompatibles | 2 | 41% Omafilcon 59% Water |
| RYTHMIC ® | Essilor | 2 | 27% MMA-NVP 73% Water |
| SB 60+ ® | Bourgeois | 2 | 40% HEMA-GMA 60% Water |
| SATUREYES ® | Metro Optics | 2 | 45% Hioxifilcon A 55% Water |

[a]FDA Group 4: high water content/ionic.
FDA Group 2: high water content/non ionic
MMA = methylmethacrylate-N-vinylpyrolidone
GMA = glycerol methacrylate Since small proteins like lysozyme can penetrate the hydrogel matrix, protein adsorption level relative to the mass, rather than the surface area, of the contact lens or hydrogel material was measured. Results are shown in FIG. 10B.

Figure 10B:
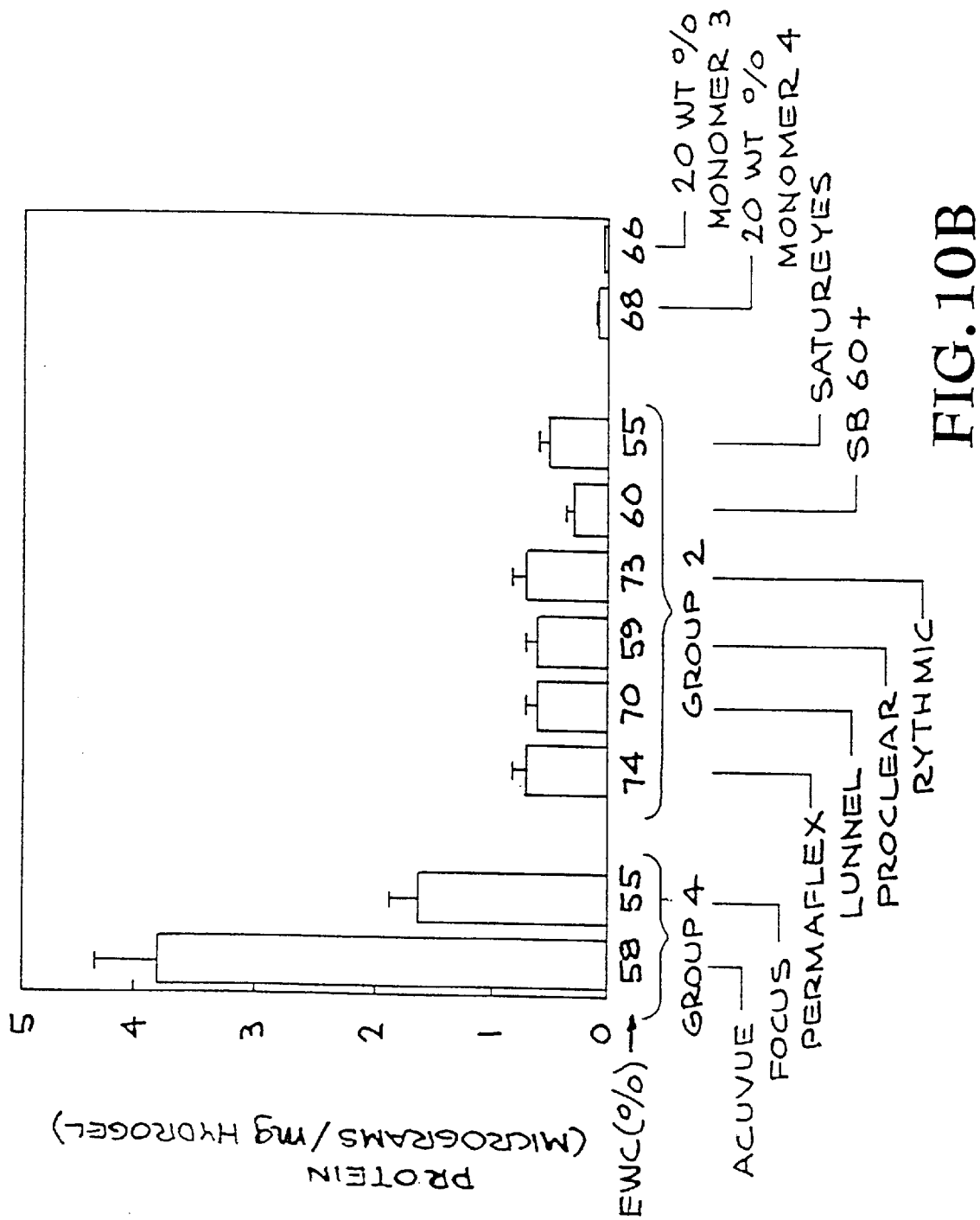
FIG. 10B (micrograms/milligram of the material).

FIG. 10B shows the amount of protein bound to hydrogel pieces and contact lenses normalized for mass. The trends among Group 4 and 2 contact lenses remain more or less the same, while the relative protein adsorption to HEMA hydrogels containing 20 wt % of monomers 3 and 4 is significantly lower.

In an effort to identify physical properties of the soft contact lenses hydrogels that might correlate with protein adsorption behavior, the water binding properties these hydrogels were investigated by DSC, the surface polarity by contact angle measurement, and the surface chemical composition by XPs, using methods as described above. Additionally, the amount of free water was measured by DSC.

3. Quantification of "Free" Water by Differential Scanning Calorimetry

The water in hydrogel matrices is known to exist in thermodynamically different states. Water that is strongly associated with polymer network through hydrogen bonding and van der Waals interactions, is called the "bound or non-freezing water." Water which has a much higher mobility and weaker interactions with the polymeric environment is called the "free or freezing water".

Figure 11:
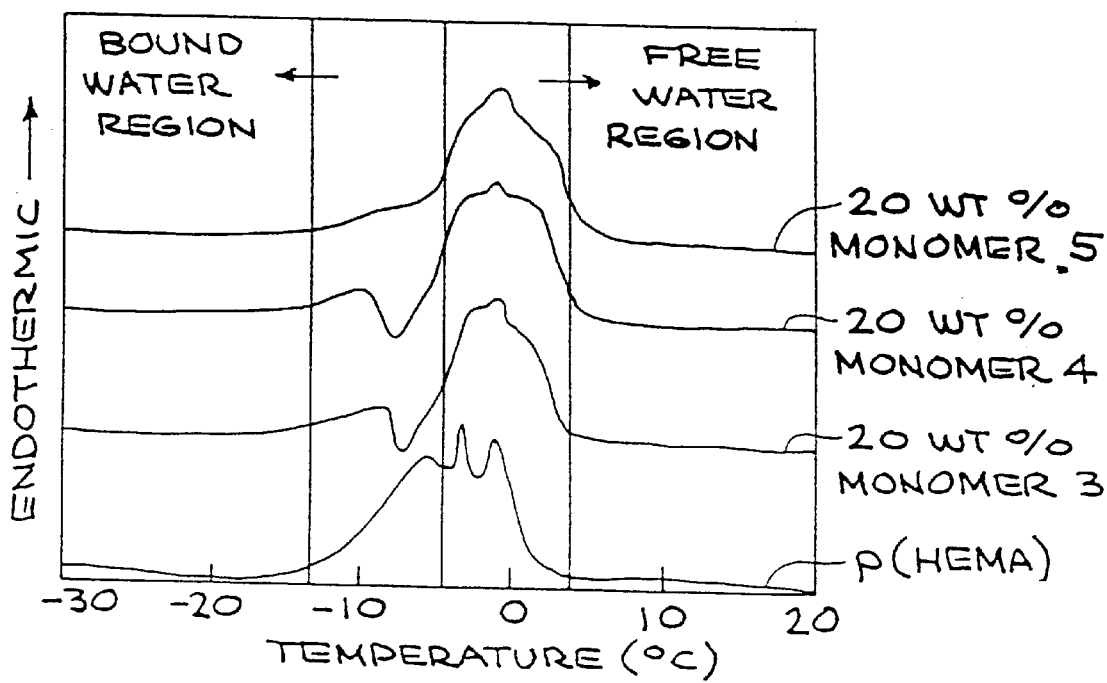
FIG. 11 shows DSC heating curves (melting endotherms of water) of hydrated HEMA-carbohydrate hydrogels containing 20 wt % of monomers 3, 4, or 5.

The differential scanning calorimetric heating curves obtained from p(HEMA) and HEMA hydrogels containing 20 wt % of monomers 3, 4 or 5 are displayed in FIG. 11. DSC shows qualitatively that for the carbohydrate-HEMA hydrogels, the amount of free water in the polymer matrix does increase significantly, along with the total amount of water (as seen in FIG. 8).

The FIG. 11 shows that, in the case of HEMA-carbohydrate hydrogels, the area under the curve representing water melting in the free water region is much higher than that for the non-freezing water regions For p(HEMA), however, a large portion of the overlapping melting curves falls in the non-freezing water region. The new hydrogels appear to hold water more tightly than p(HEMA) when heated above room temperature, based on their higher peak maximum temperatures for the water evaporation transition.

As seen in FIG. 11, incorporation of monomers 3, 4 or 5 into HEMA hydrogels enhances the amount of free water almost to equal extents. Thus, the differences in protein adsorption behavior of HEMA hydrogels comprising 20 wt % of monomers 3, 4 or 5 is not due to the amount of free water in the polymer matrix.

The HEMA-carbohydrate hydrogels of the invention used for fabrication of soft contact lenses may additionally contain pharmaceutically active compounds for therapeutic uses or additives, such as dyes, for cosmetic uses.

II. Polysulfoxide Hydrogels

The second group of novel hydrogels are hydrogels comprising sulfoxide, sulfide or sulfone-acrylated moiety copolymerized with a matrix copolymerizing material selected from the group consisting of acrylamide, methacrylamide, acrylate, methacrylate, siloxane and vinyl or their derivatized form 2-hydroxyethylacrylate (HEMA), N-vinyl-pyrrolidone (NVP), methyl methacrylate (MMA), methacrylic acid (AcM), 1,2-dihydroxy-propyl methacrylate (DPMA), glycerol methacrylate (GMA) or N,N-dimethyl acrylamide (DMA). As above, HEMA was selected as a representative testing copolymerizing material.

The sulfoxide hydrogels are cross-linked HEMA-sulfoxide (23), HEMA-sulfide (25) and HEMA-sulfone (26) hydrogels prepared by copolymerization of (3-methylsulfoxy)propyl acetate, compound 23 and its homologue, compound 24 with HEMA or by copolymerization of sulfide or sulfone with HEMA. These hydrogels are highly hydrophilic showing equilibrium water content up to 90 wt %.

Because of their improved properties, sulfoxide, sulfide or sulfone based hydrogels are suitable for fabrication of materials used for biomedical implants, such as bone, joint implant, cartilage replacement or protein-resistant soft contact lenses.

A. Sulfoxide Containing Hydrogels

Because of the presence of the highly polar, but non-ionic sulfoxide functionality in this type of hydrogels, the hydrophilicity of hydrogels generated from polymerizable sulfoxide monomers was found to be enhanced.

1. Compounds Identification

Two sulfoxide-acrylate monomers 23 and 24, seen in Chart 2, were synthesized and several of their cross-linked hydrogels with various amounts of 2-hydroxyethylmethacrylate (HEMA) were prepared.

The monomers are seen in Chart 2.

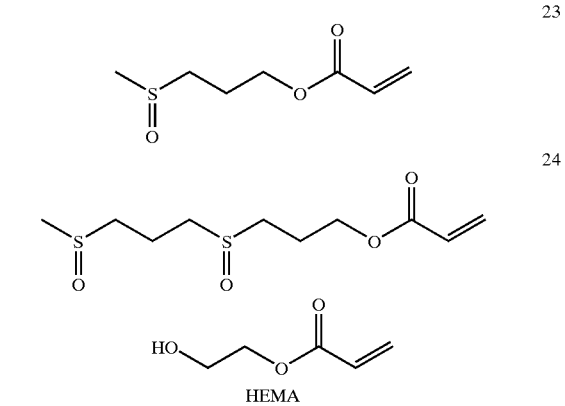

2. Synthesis of Sulfoxides

Synthesis of the sulfoxide monomers 23 and 24 is shown in Schemes 6 and Scheme 7.

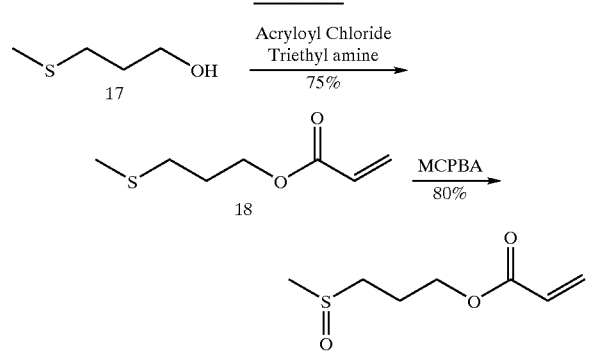

Scheme 6 illustrates preparation of sulfoxide monomer 23. As seen in Scheme 65, reaction of commercially available 3-methylthiopropanol (17) with acryloyl chloride in the presence of triethylamine gives the thioacrylate 18, that is subsequently oxidized to the corresponding sulfoxide monomer 23 with one equivalent of m-chloroperoxybenzoic acid (MCPBA).

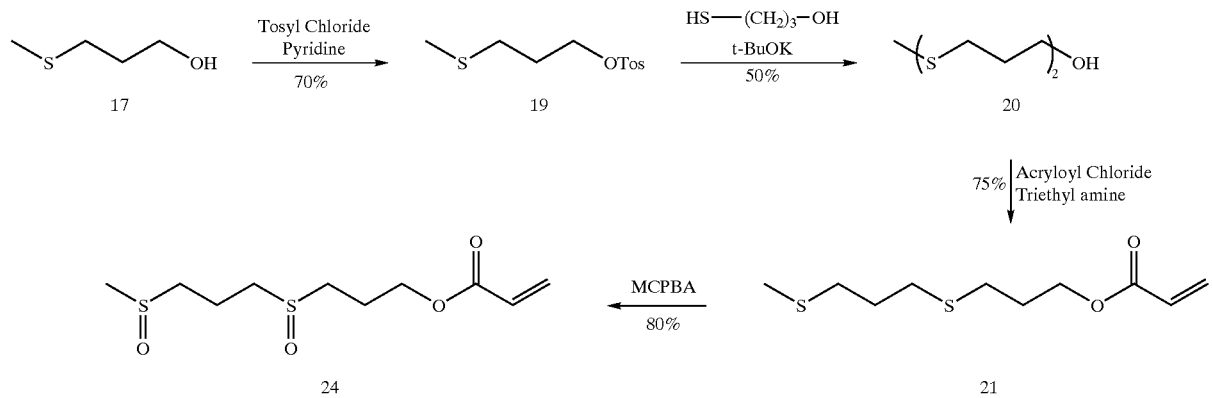

Synthesis of monomer 24 with two sulfoxide groups per acrylate moiety was accomplished by preparing the intermediate 4,8-dithianonanol 20 from 3-methylthiopropanol (17) tosylated to esterification with acryloyl chloride, followed by oxidation with m-chloroperoxybenzoic acid (MCPBA) of 20 resulted in monomer 24, as seen in Scheme 6. The preparation of compounds 23 and 24 is described in Examples 18–21.

Monomers 23 (a colorless viscous liquid) and 24 (a white low melting solid) exhibit very good solubility in HEMA. Prepolymer mixtures are prepared by combining various weight proportions of monomers 23 and 24 in HEMA with a cross-linker, such as, 1–2 wt % of ethyleneglycol dimethacrylate, a solvent, preferably ethyleneglycol/water or dimethylsulfoxide, and an initiator. The mixture is then placed between two glass plates separated by spacers to control the thickness of the product hydrogel sheets. Polymerizations are initiated either thermally with ammonium persulphate or photochemically with benzoin methyl ether and applying of light of 365 nm wave length. The hydrogel sheets thus obtained are hydrated and washed in deionized water for several days to remove the extractable monomers, oligomers and solvents.

The sheets are then cut into 1×1 cm² pieces, stored under deionized water and tested for their physical and biological properties.

3. Physical Properties of Sulfoxides i. EWC of Sulfoxide-HEMA Hydrogels

The fundamental property of hydrogels is their ability to hold water in their cross-linked polymer matrix. Pure HEMA hydrogels at 1–2 wt % cross-linking levels typically exhibit an equilibrium water content of about 40 wt % at room temperature as described above. Incorporation of hydrophilic sulfoxide functionality into HEMA hydrogels has resulted in a significant enhancement of water content. Results are seen in FIG. 12.

Figure 12:
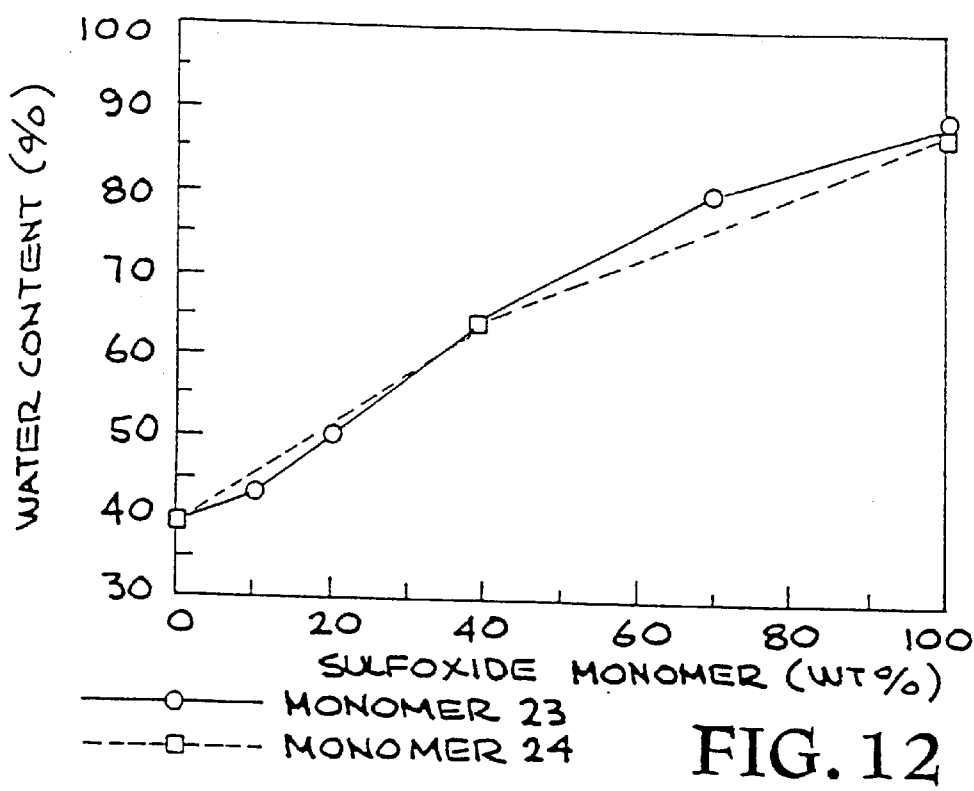
FIG. 12 illustrates an effect of sulfoxide concentration (wt %) on the equilibrium water content (wt %) in HEMA-sulfoxide hydrogels.

FIG. 12 shows the effect of sulfoxide monomer(s) 23 and 24 concentration in the hydrogel on the equilibrium water content of the hydrogel. When the concentration of monomer 23 in HEMA is increased from 0–100 wt %, the water content of the resulting hydrogels goes up from 40 to about 90 wt %. A similar behavior is also noted for the monomer 24.

ii. Water Retention in Sulfoxide-HEMA Hydrogels

The water retention ability of the sulfoxide containing hydrogel systems was measured by differential scanning calorimetry (DSC). DSC measures the water evaporation from the polymer matrix and records this irreversible transition as a broad peak in the DSC thermogram. The peak maximum temperature (PMT) is taken as a qualitative measure of the water retention ability of the hydrogel system wherein the higher PMT indicates the stronger water retention in the polymer matrix. The DSC peak maximum temperatures of various mixed sulfoxide-HEMA hydrogels are given in FIG. 13.

Figure 13:
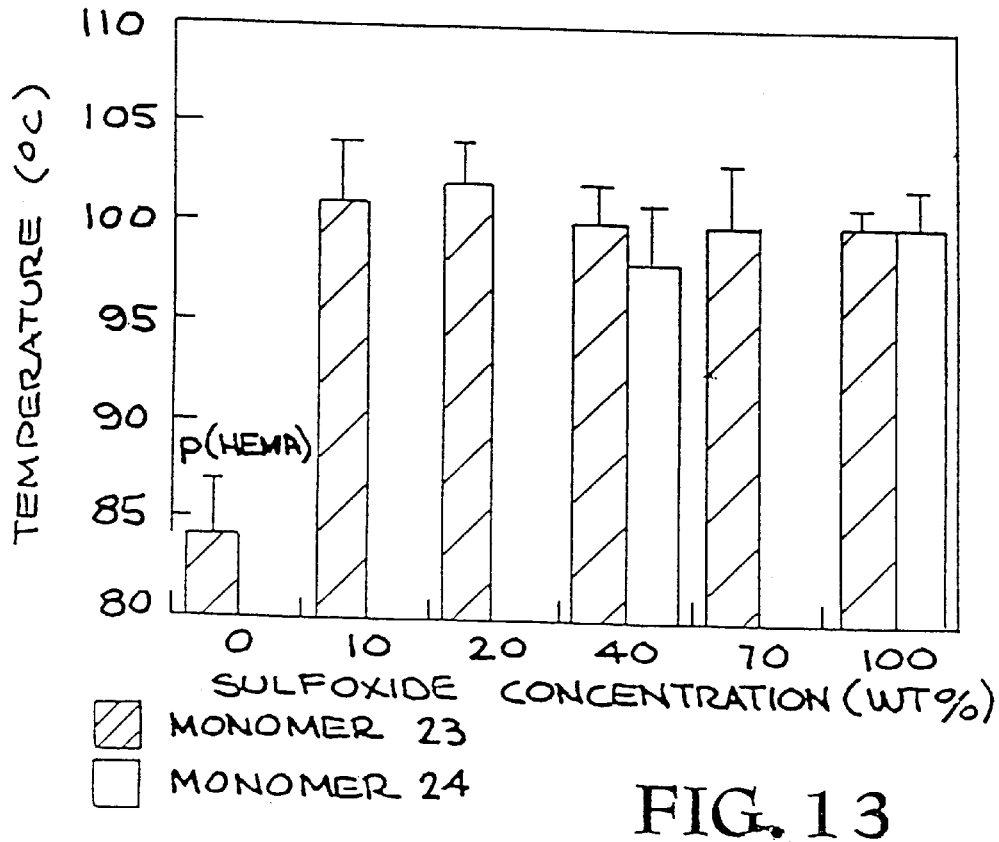
FIG. 13 shows an effect of sulfoxide concentration (wt %) on the DSC peak maximum temperatures (° C.) of the HEMA-sulfoxide hydrogels.

FIG. 13 shows that the mixed hydrogels containing hydrophilic sulfoxide functionality exhibit much higher peak maximum temperatures than pure HEMA hydrogels and are therefore more hydrophilic.

4. Biological Properties of Sulfoxides

A. Sulfoxide-HEMA Hydrogels and In Vitro Protein Adsorption Study

The development of the new sulfoxide-based hydrogel systems was based on the hydrophilic nature of the sulfoxide moiety which enhances the equilibrium water contents and on its protein repelling ability.

Studies described above for HEMA-carbohydrates of the in vitro protein adsorption behavior of carbohydrate-derived hydrogels systems using artificial tear fluid utilized a mixture of proteins and lipids that are commonly found in human tears. The same experimental conditions were used for determination of biological properties of sulfoxide containing hydrogel.

As described above, the test involves incubation of hydrogel pieces in ATF at physiological pH (7.24) and temperature (37° C.) for a given period of time and the determination of the amount of protein adsorbed on the polymer surface. BCA assay was used for protein quantification. The results of the study are presented in FIG. 14.

Figure 14:
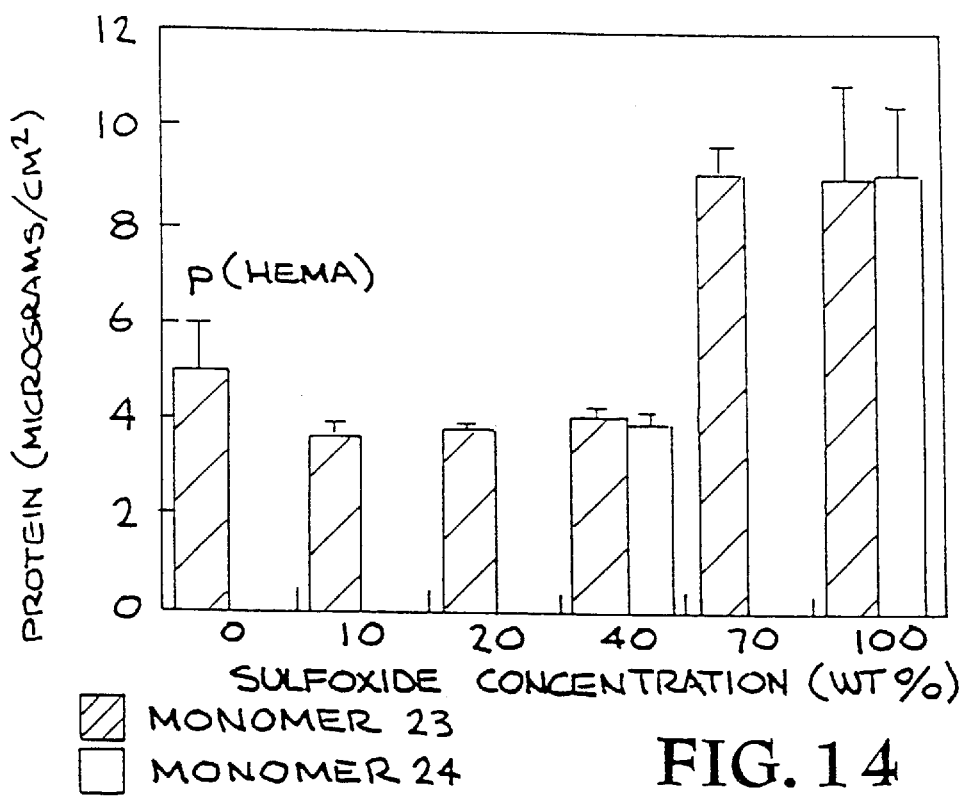
FIG. 14 shows an effect of sulfoxide concentration (wt %) on the amount of proteins adsorbed on HEMA-sulfoxide hydrogels before and after incubation in artificial tear fluid for 24 hours at 36° C.

FIG. 14 shows results from in vitro protein adsorption study wherein the amount of surface-bound proteins for mixed hydrogels was found to be lower or about the same as that of p(HEMA) hydrogels when. the sulfoxide concentration was maintained between 10–40 wt %. At higher sulfoxide concentrations (70 and 100 wt %) present within the hydrogel, the amount of proteins adsorbed on the HEMA-sulfoxide hydrogel surfaces was about twice that of the pure HEMA hydrogels.

The systems where equilibrium water content is enhanced to about 70 wt % without compromising the protein repelling ability are sulfoxide-derived HEMA hydrogels containing up to 40 wt % of sulfoxide. Results are seen in FIG. 15 in which the sulfoxide concentration is plotted against equilibrium water contents and amount of surface bound proteins.

Figure 15:
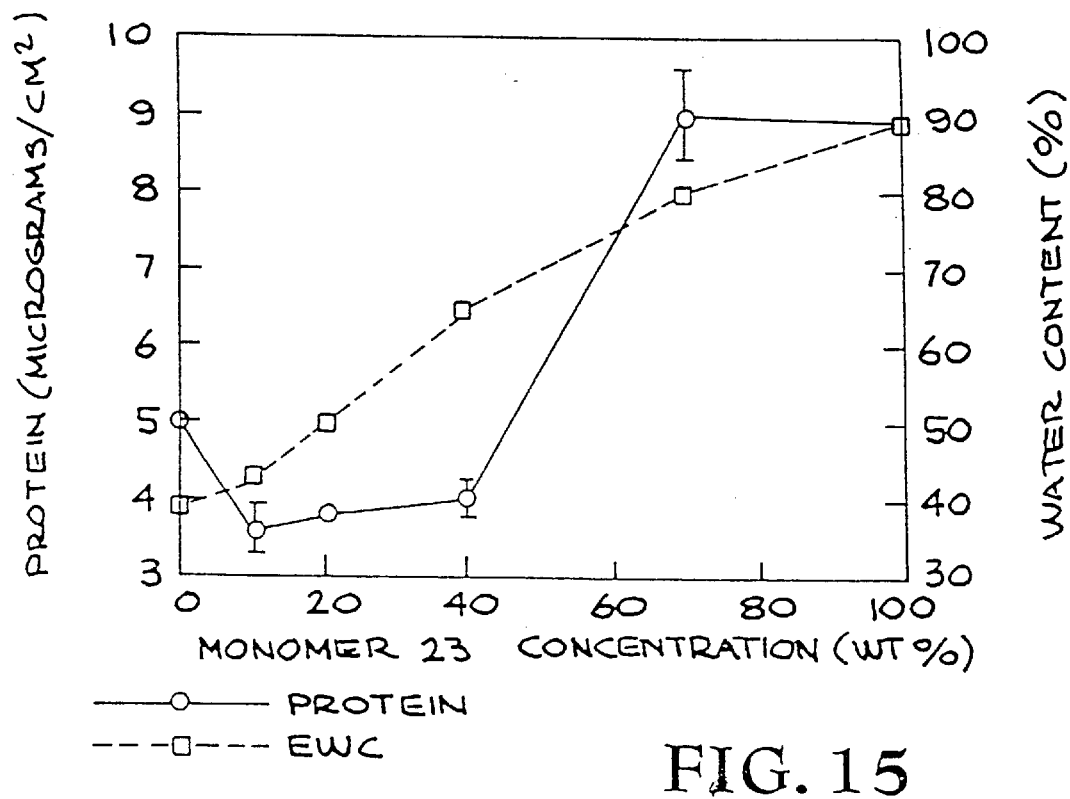
FIG. 15 shows an effect of sulfoxide concentration (wt %) on the equilibrium water content (wt %) and on the amount of protein adsorbed after 24 hours incubation in ATF at 36° C.

As seen in FIG. 15, when the concentration of sulfoxide 23 is between 10 and 40 wt %, the water content is increased up to about 70 wt % and the protein adsorption is much lower than the adsorption of p(HEMA). However, the presence of sulfoxide above about 60 wt % sharply increases the protein adsorption.

Copolymerization of compounds 23 and 24 with HEMA produces hydrogels having much higher water uptake than p(HEMA) hydrogels, while maintaining similar or much lower levels of in vitro protein adsorption. The sulfoxide-based hydrogels constitute promising new materials particularly for use in biomedical implant applications and soft contact lens applications in particular.

B. Sulfide- and Sulfone-Derived Mixed Hydrogels

The above results show the effects of incorporating sulfoxide functionality in HEMA-based hydrogels on improving the properties of the hydrogels, such as water content, reduced protein adsorption, etc. Consequently, based on these findings, the effect of oxidation state of the sulfur in sulfur-based new acrylate monomers was investigated to determine if incorporation of other sulfur compounds into hydrogels may have similar properties. This investigation was directed to monomers 25 and 26 seen in Chart 3 and on what properties they impart on hydrogels when they are copolymerized with HEMA.

1. Compounds Identification

Two acrylate monomers, sulfide acrylate (25) and sulfone acrylate (26) were synthesized and copolymerized with HEMA. The acrylate monomers 25 and 26 are seen in Chart 3.

CHART 3

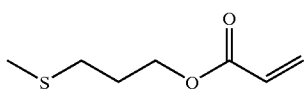

25

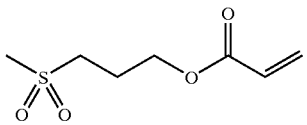

Compound 25 sulfide, compound 26 is sulfone. These monomers are less and more oxidized, respectively, with respect to the corresponding sulfoxide (monomer 23). Their polarity or hydrophilicity decreased in the order of sulfoxide 23>sulfone 26>sulfide 25.

2. Synthesis of Sulfide and Sulfone Hydrogels

Synthesis of 25 and 26 is seen in Scheme 7. The synthesis involves one step esterification of commercially available 3-methylthiopropanol 17 with acryloyl chloride to sulfide 25. Double oxidation of monomer 25 with two equivalents of m-chloroperoxybenzoic acid results in the formation of monomer 26 (Scheme 8).

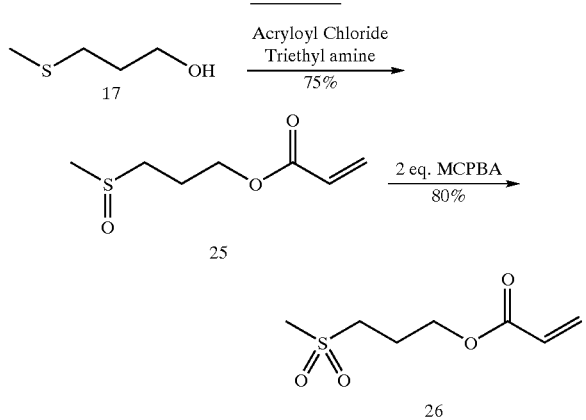

Figure 17A:
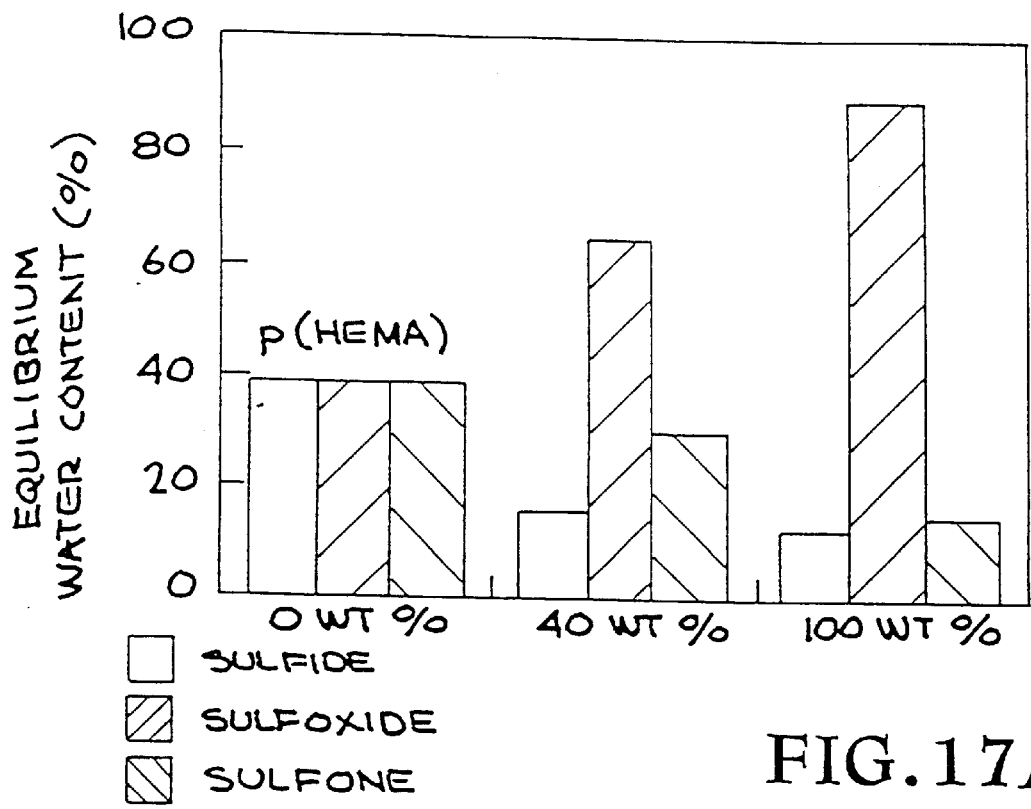
FIG. 17 shows an effect of concentration (wt %) of sulfide, sulfoxide or sulfone in HEMA-sulfide, HEMA-sulfoxide or HEMA-sulfone on the equilibrium water contents of the corresponding hydrogels (FIG. 17A) or on in vitro protein adsorption on the corresponding hydrogels after incubation in artificial tear fluid for 24 hours at 36° C.
(FIG. 17B). The equilibrium water contents (EWC, wt %) of the hydrogels are depicted at the bottom of each bar.

B. Hydrophilicity and In Vitro Adsorption of Sulfide- and Sulfone-HEMA Hydrogels The sulfide 25 and sulfone 26 acrylates were then copolymerized with HEMA or other hydrophilic or hydrophobic copolymerizing material, as identified above, according to the procedure outlined above for the hydrogels of 23 and 24. The equilibrium water contents of the hydrogels 25 and 26 were measured and compared to that of corresponding hydrogels of their sulfoxide analogue 23. Results are seen in FIG. 17A.

The equilibrium water contents of the sulfide, and sulfone-HEMA hydrogels are rather low compared with the sulfoxide hydrogels. In fact, the mixed hydrogels become more hydrophobic than the pure HEMA hydrogels themselves as the amount of monomers 25 or 26 increases in the hydrogel. This trend is based on the respective polarities of monomers 23, 25 and 26.

C. In Vitro Protein Adsorption of the Sulfoxide-, Sulfide- or Sulfone-HEMA Soft Contact Lenses The improved characteristics of the sulfoxide-, sulfide- or sulfone-HEMA hydrogels led to fabrication of soft contact lenses using these materials. Sulfoxide containing hydrogels resulted in. contact lenses with good tensile strength and high equilibrium water contents of approximately 65–80 wt %. The in vitro protein adsorption behavior of the sulfoxide-derived contact lenses have been measured, and compared to various commercial soft lenses. For this purpose, three different materials denoted formulations F1, F2 and F3 were prepared and compared to commercially available lenses that belong to high water content-ionic (FDA Group 4) and high water content-nonionic (FDA Group 2). The results of this study are presented in FIG. 16.

Figure 16:
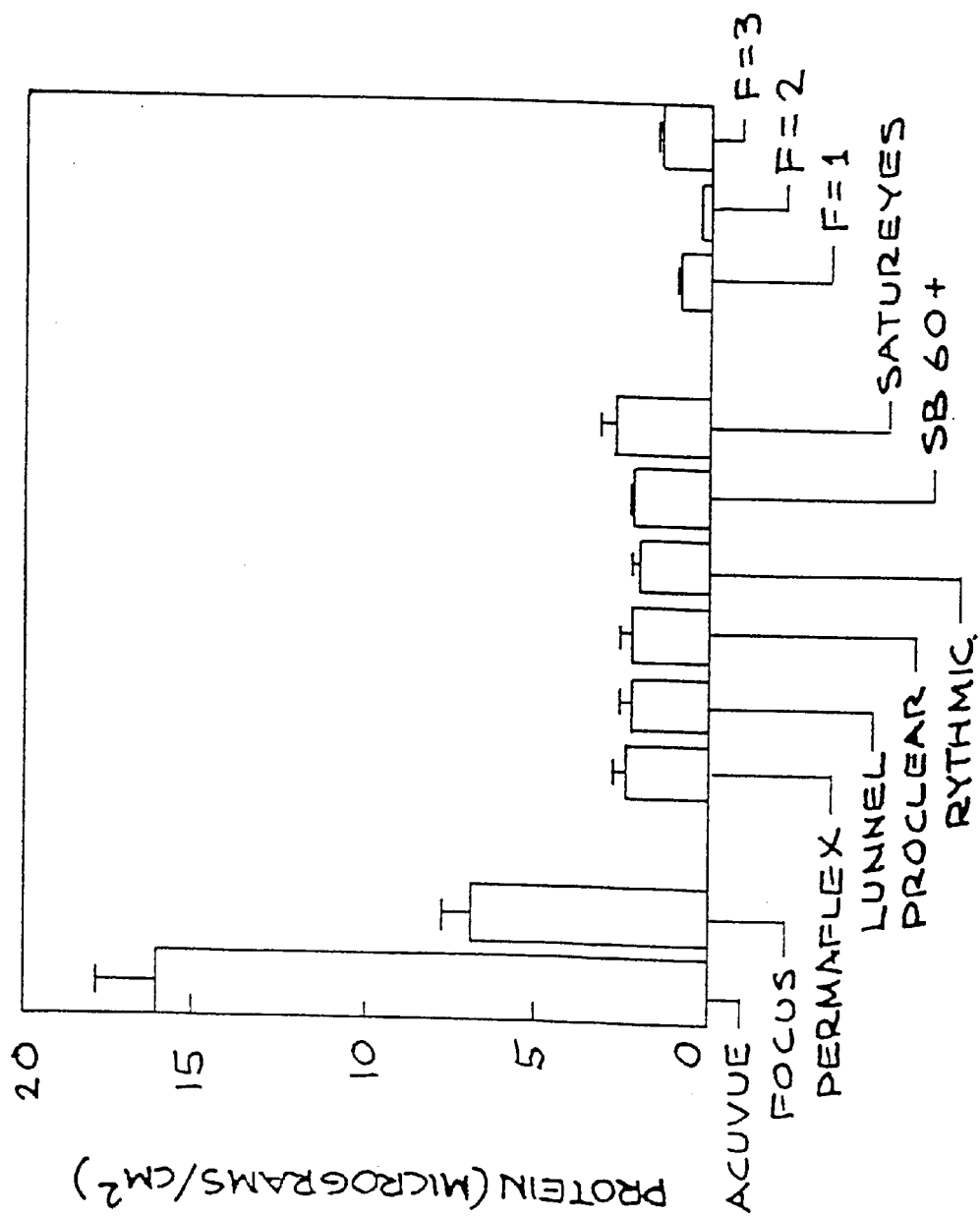
FIG. 16 shows a protein adsorption (micrograms/cm$^2$) on hydrogel materials of various commercially available contact lenses and on lenses made of three different HEMA-sulfoxide formulations (F-1, F-2 and F-3) during 24 hours incubation in artificial tear fluid at 36° C.

In FIG. 16, ACUVUE®, and FOCUS® ionic lenses of Group 4 showed high levels of protein adsorption. Lenses made of PERMAFLEX®, LUNNELLE®, PROCLEAR®, RYTHMIC®, SB 60+® and SATUREYES® (FDA Group 2) had considerably lower levels of protein adsorption than the ionic lenses. The lowest levels of adsorption was observed for three formulations (F-1, F-2 and F-3) of HEMA contact lenses containing 27 wt % of sulfoxide 23 and 73 wt % of combination of HEMA (71–72.9 wt %) a cross-linker (0.1×2 wt %), and additives (negligible amounts) that improve the physical properties of the hydrogel but do not affect protein binding. Toxicological tests on the sulfoxide-HEMA hydrogels revealed no toxicity of the new hydrogels.

Figure 17B:
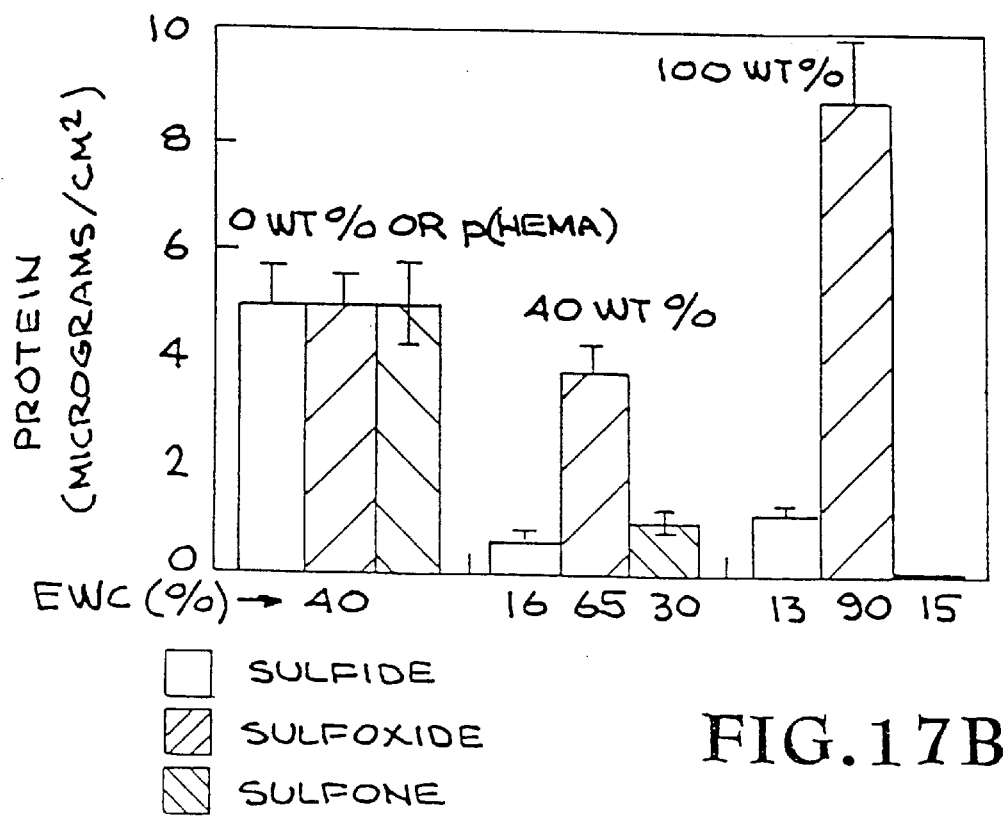

In the in vitro protein adsorption study of sulfide and sulfone containing hydrogels compared to that of sulfoxide hydrogels showed that the protein adsorption is lower for both sulfide- and sulfone-HEMA hydrogels compared to the sulfoxide derivatives. The results are presented in FIG. 17B, which shows the equilibrium water content of these hydrogels vis-a-vis their protein adsorption.

In spite of their lower protein adsorption, the mixed hydrogels of HEMA containing monomers 25 and 26 will probably not be as useful as the carbohydrate or sulfoxide containing hydrogels for soft contact lens applications due to their very low hydrophilicity. However, based on their other properties, they can be used as other biomedical implant materials, as transdermal patches, delivery vehicles, joint, bone implants etc., where high water content is not as crucial and/or desirable as is their low protein binding characteristics. This is especially true for the sulfone-HEMA hydrogels.

UTILITY

Hydrogels of the invention are suitable for extensive applications as biocompatible synthetic materials, in such diverse devices as drug delivery vehicles, artificial muscle, collagen replacement implants, contact lenses and such others.

One of the most crucial characteristics and requirements for biomedical implant materials is their biocompatibility, that is, the lack of adverse effects on biological tissue at the material interface. Biocompatibility is closely governed by surface bioadhesion and adsorption of proteins is among the first observable events that occurs on a material's surface when it comes in contact with biological fluids such as blood, plasma and tear fluid. A degree of initial protein adsorption on the hydrogel surfaces leads to provoking secondary events, such as cell and bacterial adhesion to the hydrogel. Adhesions of cells or bacteria can compromise the proper function of biomedical implants.

Contact lenses made from the current hydrogels possess desirable properties such as softness and flexibility to be comfortable to the eye, and most importantly, permeability to oxygen. These characteristics depend on the degree of hydration of the hydrogel matrix. Because contact lenses are prone to deposition of undesirable proteins and lipids on their surfaces from the surrounding tear fluid, high hydrophilicity and low protein adsorption are the two most sought after properties of hydrogel materials suitable for soft contact lens applications.

Previously used poly(2-hydroxyethyl methacrylate) [p(HEMA)], hydrogels are the optimal choice because of their combination with carbohydrates for contact lens fabrication because of their inherently low protein binding nature and excellent physical properties including optical clarity and high tensile strength. Unfortunately, alone they have relatively low water uptake and oxygen transmissibility, the two features that must be improved for better performance. Incorporation of carbohydrate, sulfoxide, sulfide or sulfone groups, according to the invention enhances the equilibrium water content of poly(HEMA) hydrogels making them more resistant to protein adsorption, resulting in highly hydrophilic hydrogels.

Increased water content, hydrophilicity and low protein adsorption of HEMA-based hydrogels are the important features of the invention, particularly useful for the soft-contact lens materials, since higher equilibrium water content results in better oxygen supply to the cornea.

On the other hand, the hydrogels containing higher sulfoxide concentration, (approximately 70 wt %) which have very high water contents, possess very low tensile strengths and are therefore not particularly suitable to be used for contact lens fabrication. Such super absorbent-like hydrogel materials are, however, useful for other biomedical applications as artificial joint implants, intraocular lenses etc.

EXAMPLE 1

General Procedures, Methods and Materials

Unless otherwise noted, all reagents used for preparation and testing of hydrogels were obtained from commercial suppliers (Aldrich) and were used without further purification. Reagent grade solvents were from Fisher or EM Sciences companies.

2-Hydroxyethyl methacrylate (HEMA) was purified by distillation under reduced pressure prior to use.

Deionized water used in experimental manipulations was ultrafiltered using a Millipore Milli-Q UF Plus water purification system.

$^1$H and $^{13}$C NMR spectra were recorded on a Varian XL-200 spectrometer at 200 MHZ for protons and 50 MHZ for carbons respectively.

Proton spectra were referenced to the relevant residual solvent resonance ($\beta$=2.50 ppm for DMSO-d6 or internal Si(CH$_3$)$_3$ when obscured).

Carbon spectra were referenced to the relevant solvent resonances ($\beta$=39.50 ppm for the center line of DMSO-d6).

Lysozyme (~95 wt %, from chicken egg white), albumin (96 wt %), bovine) and mucin (type III, from porcine stomach) were all purchased from Sigma.

Phosphate buffer saline (PBS) solution was made from PBS tablets (Sigma) dissolved in deionized water.

BCA protein assay kit (#22325) was purchased from Pierce (Rockford, Ill.).

Various brands of commercial soft contact lenses were gifts from Sunsoft Corporation, (Albuquerque, N. Mex., USA) and Essilor corporation, (Paris, France). The details of the chemical composition are given in Table 3.

Absorption spectra were recorded on a Shimadzu UV-1601 spectrophotometer.

Static contact angles of diiodomethane (99 wt %, Aldrich, 3 microliter droplets) on dry hydrogels in air or on hydrated hydrogels immersed in water were measured using a goniometer (model #100-00115, Rame-Hart, Inc., Mountain Lakes, N.J.).

EXAMPLE 2

N-Methyl-N-$\beta$-rhamnosyl Acrylamide (1)

Methylamine hydrochloride (3.8 g, 56.3 mmol) was added slowly to a fresh prepared solution of NaOMe in methanol (100 mL, 1.0 M) and the precipitates were removed by gravity filtration. L-rhamnose monohydrate (5.1 g, 28.0 mmol) was then added and the solution was stirred at room temperature overnight. The reaction mixture was evaporated to dryness to give the light yellow solid intermediate compound 6 which was used for the next step without further purification. To the solid intermediate were slowly added 500 mL of methanol, 30 mL of triethylamine, and a solution of acryloyl chloride in THF (80 mL, 25 wt % vol/vol). The solution was maintained at ambient temperature. The reaction mixture was stirred for 4 hours at room temperature, concentrated in vacuo, and diluted with 100 mL of triethylamine. The precipitated solids were removed by vacuum filtration, and the filtrate was concentrated and purified by silica gel chromatography eluting with 6:1 ethyl acetate/methanol to give 3.1 g (49 wt %) of monomer 1.

Monomer 1 exists as a mixture of rotamers around the tertiary amide at room temperature.

NMR spectra were recorded at a temperature above the coalescence point to simplify peak assignments. $^1$H NMR (200 MHZ, DMSO-D$_6$, 130° C.): $\delta$6.65 (dd, J=16.8, 10.6 Hz, 1H, —C$\underline{H}$=), 6.06 (dd, 1H, J=16.7, 2.4 Hz, =C$\underline{H}_2$), 5.62 (dd, J=10.5, 2.3 Hz, 1H, =C$\underline{H}_2$) 5.24 (s, 1H, —C$\underline{H}$OH), 4.28–4.10 (m,2H, —C$\underline{H}$OH), 3.82 (s, broad, 1H, —C$\underline{H}$OH), 3.24–3.40(m, 1H, —C$\underline{H}$CH$_3$), 3.05 (s, 3H, —NC$\underline{H}_3$), 2.88–2.80 (m, 1H, 1.22, —C$\underline{H}$OH), 1.23(d, J=5.8 Hz, 3H, —C$\underline{H}_3$); $^{13}$C NMR (50 MHZ, DMSO-d$_6$ 130° C.): $\delta$17.11, 29.72, 71.04, 71.32, 74.06, 81.67, 125.34, 128.97, high resolution mass spectrum (FAB$^+$) calcd for C$_{10}$H$_{17}$O$_5$N 232.1185, found 232.1181.

EXAMPLE 3

2,3,4,5-Tetra-O-Acetyl-N-Allyl-$\beta$-N-Xylosyl Acetamide (7)

For preparation of compound 7, which is an intermediate for preparation of monomer 2, D-xylose (4.0 g, 26.7 mmol) was stirred in allylamine at room temperature for 24 hours. The solution was evaporated in vacuo and the residue was treated with acetic anhydride/pyridine (1:1; vol/vol) overnight. The solution was evaporated to dryness to give 9.3 g (98 wt %) of product compound 7, as slightly colored solid. $^1$H NMR (200 MHz, DMSO-d$_6$, 130° C.) : $\delta$5.85–5.64 (m, 1H, —C$\underline{H}$=CH$_2$), 5.50 (d, 1H, J=9.1 Hz, —OC$\underline{H}$N), 5.28 (dd, 1H, J=9.3, 9.5 Hz, —C$\underline{H}$OAc), 5.18–4.88 (M, 4H, —C$\underline{H}$OAc, =CH$_2$), 4.00 (dd, 1H, J=11.5, 6.2 Hz, —CH$_2$—), 3.92–3.83 (m, 2H, —C$\underline{H}_2$CH=CH$_2$), 3.58 (dd, 1H, J=11.2, 10.7 Hz, —CH$_2$—), 2.05 (s, 3H), 1.98 (s, 3H) 1.95 (s, 3H), 1.92 (s, 3H); $^{13}$C NMR (50 MHz, DMSO-d6, 130° C.): $\delta$20.02, 21.59, 44.75, 64.19, 68.71, 69.27, 73.23, 83.47, 115.78, 135.37, 168.70, 169.13, 169.17, 170.55.

EXAMPLE 4

N-[Allyl-]-$\beta$-N-Xylosyl Acetamide (8)

For preparation of the second intermediate for synthesis of monomer 2, compound 7 (9.3 g, 26 mmol) was dissolved in methanol and treated with an aqueous solution of sodium methoxide in methanol until pH 9 was reached. The solution was stirred at room temperature for 4 hours. Dowex resin (H+ form) was used to neutralize the solution to give deacetylated product 8 and the solution was filtered and concentrated in vacuo. Compound 8 was obtained in quantitative yield as an oily residue. $^1$H NMR (200 MHz, DMSO-d$_6$, 130° C.): $\delta$5.94–5.72 (m, 1H, —C$\underline{H}$=CH$_2$), 5.15 (dddd, 1H, J=17.4, 1.7, 1.7, 1.7 Hz, —CH=C$\underline{H}_2$), 5.01

(dddd, 1H, J=10.3, 1.7, 1.7, 1.7 Hz, —CH=CH$_2$), 4.88 (app d, 1H, J=7.5 Hz, —OCHN), 3.98–3.84 (m, 2H, —CH$_2$CH=CH$_2$), 3.80–3.72 (m, 2H, —CHOH), 3.38–3.20 (m, 3H, —CHOH, —CH$_2$—), 2.05 (s, 3H); $^{13}$C NMR (50 MHz, DMSO-d6, 130° C.): δ21.59, 44.03, 60.00, 68.02, 69.64, 70.49, 78.11, 115.06, 136.23, 170.02.

EXAMPLE 5

N-[3-(2-N'-Ethyl Propenamido)Thiopropyl]-β-N-xylosyl Acetamide (2)

Cysteamine (2-amino ethanethiol hydrochloride) (3.2 g, 28.2 mmol) and the deacetylated compound 8 were dissolved in 15 mL of deoxygenated water. This solution was purged with nitrogen and irradiated with ultraviolet light (254 nm) under nitrogen atmosphere for 5 hours until complete disappearance of the starting material. The solution was evaporated to dryness and the product compound 9 was then used without further purification.

Monomer 2 was prepared by dissolving the amine 9 (26.0 mmol based on the moles of compound 6) in methanol and acryloylated by a slow dropwise addition of acryloyl chloride (10 mL, 123 mmol) in THF (18 wt %; vol/vol) at 0° C. The pH was maintained between 8–9 with 2M KOH. The solution was neutralized with cation exchange resin (DOWEX resin H+ form) to give crude product 2. Silica gel column chromatography purification with 4:1 ethylacetate/methanol gave 5.8 g (62 wt %) of pure monomer 2 as a hygroscopic solid. At room temperature, compound 2 existed as a mixture of rotamers around the tertiary amide.

NMR spectra were recorded at a room temperature above the coalescence point to simplify peak assignments.

$^{1}$H NMR (200 MHZ, DMSO-d$_6$ 130° C.): 6.22 (dd, J=17.0, 9.7 Hz, 1H, =CH, 6.06 (dd, 1H, J=17.1, 2.5 Hz, =CH$_2$), 5.53 (dd, J=9.8, 2.6 Hz, 1H, =CH$_2$), 4.78 (d, 1H, J=8.5 Hz, —CHOH), 3.82–3.72 (m, 2H, —CHOH), 3.27–3.44 (m, 3H, —CH2, —CHOH), 3.28–3.10 (m, 4H, —CH$_2$) 2.54 (t, J=7.3 Hz, 2H, —CH$_2$), 2.06 (s, 3H, —CH$_3$), 1.81 (m, 2H, —CH$_2$); $^{13}$C NMR (50 MHZ, DMSO-d$_6$, 130° C.): δ20.92, 28.67, 28.74, 30.46, 67.45, 69.07, 69.86, 77.51, 77.56, 114.45, 123.55, 131.44, 164.29, 170.11; high resolution mass spectrum (FAB$^+$) calcd for C$_{15}$H$_{26}$O$_6$N$_2$S 363.1590, found 363.1584.

EXAMPLE 6

N-Acryloyl-D-Glucamine (3)

N-Acryloyl-D-glucamine (3): 1-Amino-1-deoxy-D-sorbitol (D-glucamine) 10 (5.0 g, 28 mmol) was dissolved in a mixture of CH$_3$OH (120 mL) and H$_2$O (15 mL) and cooled in an ice bath. Acryloyl chloride (30 mL of a 2.35 M solution in THF, 71 mmol) was added dropwise to. the above solution, while the pH of the reaction mixture was maintained between 8 and 9 by periodic addition of 2M aqueous KOH. After an additional 1-h period on ice, the volatiles were evaporated under reduced pressure and the residue was subjected to silica gel chromatography with a gradient of 5–15% CH$_2$Cl$_2$ in MeOH to give 3.6 g (56%) compound 3 as a white solid; mp 122–123° C.

$^{1}$H NMR (400 MHZ, D$_2$O): δ6.38–6.22 (m, 2H, =CH$_2$, 5.80 (d, 1H, J=10.1 Hz, =CH), 3.88–3.27 (m, 8H, —CH—OH, —CH$_2$OH and NCH$_2$—); $^{13}$C NMR (100 MHz, D$_2$O)): δ171.53, 132.61, 130.29, 74.09, 73.78, 73.03, 65.51, 44.74; anal. calcd for C$_9$H$_{17}$O$_6$N: C, 45.95; H, 7.29; N, 5.96. Found: C, 45.74; H, 7.27; N, 6.08.

EXAMPLE 7

N-Acryloyl-N-Methyl-D-Glucamine (4)

For preparation of monomer 4, N-methyl-D-glucamine (5.0 g, 25.5 mmol) was dissolved in a mixture of methanol (120 mL) and water (15 mL), and cooled to 0–5° C. on an ice bath. Acryloyl chloride (2.35M in THF, 30 mL, 70.5 mmol) was added dropwise to the above solution, while pH of the reaction mixture was maintained at 8–9 by periodic addition of 2M aqueous KOH. The mixture was stirred for an additional hour at 0–5° C., the volatiles were evaporated under reduced pressure and the residue was subjected to column chromatography (silica gel, 5–15 wt % CH$_2$Cl$_2$ in MeOH) to afford a white solid compound 4 (4.35 g, 69 wt %).

$^{1}$H NMR (200 MH2, DMSO-d$_6$, 130° C.) δ6.72 (dd, 1H, J=160, 12.0 Hz, =CH), 6.04 (dd, 1H, J=16.0, 2.5 Hz, CH$_2$), 5.57 (dd, 1H, J=12, 2.5 Hz, =CH$_2$), 4.10–3.76 (m, 5H, —CH—OH), 3.66–3.36 (m, 8H, —CH—OH, —CH$_2$OH and N—CH$_2$—), 3.01 (s, 3H, —NCH$_3$); $^{13}$C NMR (50 MHZ, DMSO-d6, 130° C.): δ166.1, 129.4, 125.4, 72.4, 72.0, 71.2, 70.2, 63.4, 51.8, 35.1; IR (KBr): 3380, 2879, 1648, 1510 cm$^{-1}$; high resolution mass spectrum (FAB$^+$) calcd for C$_{10}$H$_{20}$O$_6$N 250.1288, found 250.1290.

EXAMPLE 8

3,6,9-Trioxadecane-1-Tosylate (12)

p-Toluenesulfonyl chloride (26.0 g, 136 mmol) was added in portions to a cold (0° C.) mixture of 3,6,9-trioxadecane- 1-ol, dry pyridine (15.3 g, 194 mmol) and dry $CHCl_3$ (120 mL) with vigorous stirring. After the reaction mixture was stirred at 0° C. for 2.5 h, $H_2O$ (100 mL) was added and the product was extracted with ether (150 mL). The organic layer was washed successively with 150 mL of 2N HCl, $H_2O$ saturated aqueous $NaHCO_3$, and $H_2O$, and then dried over $Na_2SO_4$. The solution was concentrated and the product was purified by silica gel chromatography with 10% ethyl acetate in hexanes followed by 100% ether, affording pure compound 12 (25 g, 86%) as a colorless oil.

$^1$H NMR (200 MHZ, $CDCl_3$): 7.78 (d, J=8.5 Hz, 2H, aromatic), 7.32 (d, J=8.5 Hz, 2H, aromatic), 4.15 (t, J=4.6 Hz, 2H, —C$\underline{H}_2$O$SO_2$—), 3.71–3.48 (m, 10H, OC$\underline{H}_2$C$\underline{H}_2$O—), 3.35 (s, 3H, —OC$\underline{H}_3$), 2.43 (s, 3H, Ar—C$\underline{H}_3$) IR (neat): 2980, 1608, 1110 cm$^{-1}$.

EXAMPLE 9

4-(3,6,9-Trioxa)Decyloxybenzaldehyde (13)

A mixture of 4-hydroxybenzaldehyde (2.68 g, 20.0 mmol), 3,6,9-trioxadecane-1-tosylate 12 (5.0 g, 15.7 mmol) and anhydrous $K_2CO_3$ (10.35 g, 75.0 mmol) in 2-butanone (50 mL) was heated under reflux under vigorous stirring for 5 hours. The reaction mixture was cooled to room temperature, filtered and the solid was washed with 50 mL of acetone. The combined filtrates were evaporated and the residue was subjected to column chromatography (silica gel, 50:50 wt % hexane/ether, ether and 20:50 wt % ether/acetone) to obtain a colorless oil compound 13 (3.1 g, 76 wt %).

$^1$H NMR (200 MHZ, $CDCl_3$): 9.87 (s, 1H, —C$\underline{H}$O), 7.81 (d, J=8.8 Hz, 2H, aromatic), 7.01 (d, J=8.8 Hz, 2H, aromatic), 4.20(t, J=4.5 Hz, 2H, —C$\underline{H}_2$OAr—), 3.91–3.51 (m, 10H, —OC$\underline{H}_2$C$\underline{H}_2$O—), 3.35 (s, 3H, —OC$\underline{H}_3$) ppm; IR (Neat): 2878, 1691, 1601, 1510 cm$^{-1}$.

EXAMPLE 10

N-Acryloyl-N-[4(3,6,9-Trioxa) Decyloxybenzyl]-D-Glucamine (5)

For preparation of monomer 5, sodium triacetoxyborohydride (2.6 g, 12.26 mmol) was added in one portion to a stirred mixture of 4(3,6,9-trioxa)decyloxybenzylhyde 13 (2.0 g, 7.69 mmol), D-glucamine (1.45 g, 8.0 mmol) dissolved in DMF (80 mL), and acetic acid (0.8 mL), at room temperature. The cloudy reaction mixture became clear after being stirred at room temperature for 4 hours. The addition of dry ether (300 mL) caused formation of the product, N-(4-(3,6,9-trioxa)decyloxybenzyl)-D-glucamine (14), to precipitate as a light yellow, hygroscopic solid (14) that was filtered, washed with more ether (50 mL), suction dried, and used in acryloylation without further purification. The above solid 14 was dissolved in methanol (40 mL) and cooled in an ice bath at 0–5° C.

Acryloyl chloride (2.35 M in THF, 7.0 mL, 16.45 mmol) was added drop-wise to the compound 14, while the pH of the reaction mixture was maintained at pH 8–9 by periodic addition of 2M aqueous KOH. The reaction was stirred at temperature 0–5° C. for an additional 1 hour and warmed to room temperature. The residue obtained after volatiles was evaporated under reduced pressure and subjected to column chromatography (silica gel, 5–12 wt % $CH_2Cl_2$ in MeOH) to afford a colorless gum compound 5 (1.5 g, 40.1 wt % from aldehyde).

$^1$H NMR (200 MHZ, $D_2O$) δ7.14–7.03 (m, 2H, aromatic), 6.91–6.81 (m, 2H, aromatic), 6.73–6.52 (m, 1H, olefinic), 6.08 (d, J=16.6 Hz, 1H, olefinic), 5.71–5.61 (m, 1H, olefinic), 4.10–3.31 (m, 22H, —OC$\underline{H}_2$C$\underline{H}_2$O—, —N—C$\underline{H}_2$—), 3.18 (s, 3H, —OC$\underline{H}_3$); $^{13}$C NMR (200 MHZ, DMSO-d6, 110° C.) δ166.4, 130.3, 129.4, 128.5, 126.1, 114.9, 72.4, 71.9, 71.5, 71.3, 70.3, 70.0, 69.9, 69.7, 69.1, 67.7, 63.4, 57.9, 49.4; IR (Neat): 3388, 2882, 1642, 1512 cm$^{-1}$; HRMS: calcd for $C_{23}H_{38}O_{10}N$ 488.2487, found 488.2495.

EXAMPLE 11

Preparation of Copolymer Hydrogels

Equal weights of HEMA and carbohydrate monomer (4 grams each) were combined with 0.1 mL of ethylene glycol dimethacrylate (EGDMA), 1 mL of deionized water and 1.5 mL of ethylene. To this mixture were added a solution of $(NH_4)_2S_2O_8$ (400 mg/ml) and a solution of $Na_2S_2O_2$ (150 mg/mL), both in the amount of 0.5 vol/wt %. The mixture was poured onto a glass plate to form a thin 1–2 mm film and then covered with another glass plate. To obtain the even thickness film, glass pieces of 1–2 mm thickness were inserted along the edges to separate the glass plates and define the film's thickness. The polymerization reaction proceeded at room temperature overnight.

EXAMPLE 12

Copolymer Films Preparation

Typically, HEMA and carbohydrate monomer were dissolved with AIBN (1.0 wt % relative to the monomers) in dimethyl sulfoxide (DMSO) to form a 10 wt % solution. The mixture was purged with $N_2$ for 20 minutes, then heated at 65° C. under $N_2$ for 6 hours. The polymer was precipitated from solution by slow addition of acetone. The precipitated polymers were again dissolved in DMSO and cast on glass plates. Evaporation of the DMSO solution at 40° C. in vacuo afforded the copolymer films.

EXAMPLE 13

Equilibrium Water Content (EWC) Measurements

Determination of equilibrium water content was performed as follows.

After polymerization, the flat, HEMA-carbohydrate copolymer hydrogels were soaked and extracted in deionized water for 2 days at room temperature. Extraction fluid was discarded and fresh water was added two times a day each day to ensure the removal of unreacted monomers and soluble oligomers. The full hydrated samples were weighed and expressed as Wh hydrated. The obtained soft hydrogels were removed from water and dried in vacuum at room temperature for at least two days in a desiccator over phosphorous pentoxide. The dehydrated samples were weighed again and expressed as Wd (dry sample).

The amount of water content adsorbed by the hydrogel is determined from the weight of the dry polymer (Wd) and the weight of the corresponding hydrated polymer (Wh) according to the following equation:

$$EWC(\%)=[(Wh-Wd)/Wh]\times 100$$

wherein EWC is equilibrium water content; Wh is hydrated sample; and Wd is dry sample.

EXAMPLE 14

Contact Angle Measurements

The contact angles of copolymer hydrogels were measured using diiodomethane and glycerol method. Macromol. Chem. Phys., 195: 1953 (1994).

Diiodomethane and glycerol droplets were deposited on copolymer hydrogel films from casting DMSO solution were measured. For a typical copolymer film, 3 µL of diiodomethane or glycerol was dropped onto the polymer surface and static contact angle was measured within five seconds after depositing of the drop. For each sample, total six contact angle readings were collected from both sides of the droplet and the values were averaged (±2°).

EXAMPLE 15

Differential Scanning Calorimeter (DSC) Measurements

Differential scanning calorimeter measurements of the copolymer samples were performed on a Perkin-Elmer DSC-7. Fully hydrated samples of p(HEMA) and HEMA-carbohydrate polymer hydrogels were cut into 1 cm×1 cm pieces and subjected to heating between 25° C. and 150° C. at a heating rate of 5° C. per minute in a nitrogen atmosphere and DSC was performed. Spectra were recorded for all studied HEMA-carbohydrate or HEMA-sulfoxide hydrogels.

EXAMPLE 16

X-Ray Photoelectron Spectroscopy (XPS)

HEMA-carbohydrate copolymer samples were dehydrated prior to XPS analysis. The samples were dried in vacuum at room temperature for at least two days in a desiccator over phosphorous pentoxide. The XPS measurements were carried out with a Perkin-Elmer 5500 spectrometer equipped with a monochromator. The spectra were recorded with MgKα X-rays (1253.6 eV) in vacuo in the range of $10^{-8}$–$10^{-9}$ Torr.

Measurements were recorded using take-off angles of 45 degrees, with respect to the plane of the sample surfaces. The elemental compositions of C, O, N and/or S of the samples were the averaged from three detailed scan spectra. The charge correction in the binding energy scale was made by setting the —$CH_2$— peak in the carbon spectra to 285.0 eV.

EXAMPLE 17

Protein Adsorption Study

Protein absorption of HEMA-carbohydrate or HEMA-sulfoxide hydrogels was compared to the protein absorption of known materials used for contact lenses.

Artificial tear fluid (ATF), was prepared according to following procedure. Lipid mixture A (0.408 g) made from 0.4 g of triolein, 0.3 g of n-propyl oleate, 0.5 g of linalyl acetate and 0.08 g of dicaproin was added to a mixture of 0.012 g of cholesterol and 0.18 g of cholesterol linoleate and mixed thoroughly with a vortex mixer t give lipid mixture B. A portion of this mixture (0.016 g) was combined with 0.001 g of undecylenic acid, 0.4 g of lysozyme, 0.2 g of mucin, and 0.04 g of albumin, and the solid mixture was dissolved in 200 mL of 19:1 PBS/Hanks balanced salt solution under vigorous shaking. After overnight storage at 4° C., the obtained protein/lipid solution (ATF) was adjusted to pH 7.4 with 1N NaOH solution. The total protein concentration of the ATF was 3.2 mg/mL as determined using the Pierce BCA protein assay (*Macromolecules*, 26:4825 (1993)).

Individual protein solutions were made by dissolving 0.32 g of the protein in 100 mL of 19:1 PBS/Hanks balanced salt solution to a final protein concentration of 3.2 mg/mL. The protein solutions were stored at 4° C. and used within 3 weeks of their preparation.

Synthetic hydrogel pieces having 1×1 $cm^2$ area and approx. 1 mm thickness and commercial contact lenses were immersed and incubated for various time periods in ATF or in individual protein solutions (2 mL per hydrogel piece or contact lens) on a water bath maintained at 36° C. with gentle shaking. After the incubation, the hydrogels or contact lenses were removed from the protein solution, quickly rinsed in a gentle flow of distilled water, and shaken twice for about 10 minutes in 10 mL of PBS solution at room temperature.

Washed hydrogel pieces for both control and experimented materials were assayed for the presence of the adsorbed proteins using BCA protein assay reagent. In some cases, the adsorbed proteins were extracted into 1 wt % sodium dodecyl sulfate (SDS) solution (2.0 mL per lens or hydrogel piece) and optical density at 280 nm of the extract was taken as a measure of the relative adsorption levels. Results are seen in FIG. 10 for HEMA-carbohydrates and in FIG. 16 for HEMA-sulfoxide.

EXAMPLE 18

Synthesis of 3-Methylthio-1-Propyl Acrylate

To a mixture of 3-methylthio-1-propanol (17) (12.5 g, 117.7 mmol) and triethylamine (17.8 g, 177.0 mmol) in dry $CH_2Cl_2$ (110 mL) cooled in an ice bath (0–5° C.), a solution of acryloyl chloride (21.3 g, 235.0 mmol) in dry $CH_2Cl_2$ (30 mL) was added drop-wise with stirring over a period of 2.5 hours. The reaction mixture was warmed to a room temperature, and then diluted with more $CH_2Cl_2$ (225 mL) and poured into water (250 mL). The $CH_2Cl_2$ layer was washed with saturated aqueous $NaHCO_3$ solution (2×175 mL), and water (2.225 mL). Evaporation of the dried ($Na_2SO_4$) organic layer gave a yellow oil. Purification by column chromatography, (silica gel, hexanes, 10 wt % ether/hexanes) produced a clear oil compound 18 (11.4 g, 60 wt %), namely 3-methylthio-1-propyl acrylate.

$^1$H NMR (200 MHZ, $CDCl_3$); δ6.40 (dd, $J_1$=17.4 Hz, $J_2$=1.8 Hz, 1H, olefinic), 6.08 (dd, $J_1$=16.5 Hz, $J_2$=10.4 Hz, 1H, olefinic), 5.84 (dd, $J_1$=10.4 Hz, $J_2$=1.8 Hz, 1H, olefinic), 4.25 (t, J=6.3 Hz, 2H, —O$CH_2CH_2$—), 2.57 (t, J=4.0 Hz, 2H, —$CH_2CHS$—), 2.10 (s, 3H, $CH_3S$—), 1.97 (m, 2H, —$CH_2CH_2CH_2$—); IR (Neat): 1725, 1636, 1408, 1267, 1190 $cm^{-1}$; HRMS calcd for $C_7H_{12}O_2S$ 160.055802, found 160.055798.

EXAMPLE 19

Methyl 3-(Acryloyloxy)Propyl Sulfoxide

To an ice-cold solution of 3-methylthio-1-propyl acrylate (18) (5.95 g, 37.1 mmol) in $CH_2Cl_2$ (80 mL), m-chloroperoxybenzoic acid (76.5 wt % 8.37 g, 37.1 mmol) was added in portions over a period of 1.5 hours. The progress of the reaction was monitored by TLC. Upon completion of the reaction, the solvent was evaporated under reduced pressure. The resulting sticky white solid was washed with water (2×100 mL) and filtered. The water washings were evaporated under reduced pressure to yield the crude product as a yellow oil. The crude product was purified by column chromatography (silica gel, ether, 20 wt % acetone/ether, 70 wt % acetone/ether) to afford colorless oil compound 23, namely methyl 3-(acryloyloxy)propyl sulfoxide (4.3 g, 66 wt %).

$^1$H NMR (200 MHZ, CDCl$_3$): δ6.40 (dd, J$_1$=17.2 Hz, J$_2$=1.7 Hz, 1H, olefinic), 6.09 (dd, J$_1$=17.2 Hz, J$_2$=10.4 Hz, 1H, olefinic), 5.83 (dd, J$_1$=10.4 Hz, J$_2$=1.7 Hz, 1H, olefinic), 4.30 (t, J=9.8 Hz, 2H, —CH$_2$CHO—), 2.76 (t, J=7.6 Hz, 2H, —CH$_2$CH$_2$SO—), 2.58 (s, 3H, CH$_3$SO—), 2.17 (m, 2H, —CH$_2$CH$_2$CH$_2$—); IR (Neat): 1721, 1635, 1410, 1273, 1195 cm$^{-1}$; HRMS calcd for C$_7$H$_{13}$O$_3$S 177.058980, found 177.058541.

EXAMPLE 20

Large Scale Synthesis of Methyl 3-(Acryloyloxy) Propyl Sulfoxide

A mixture of 3-methylthio-1-propanol (17) (25.0 g, 235.5 mmol), triethylamine (50.0 mL, 36.3 g, 359.4 mmol) in 300 mL of dichloromethane was chilled in an ice bath and a solution of acryloyl chloride (40.0 mL, 44.6 g, 495.1 mmol) in 75 mL of dichloromethane was added drop-wise over a period of 3.5 hours with stirring, while the temperature was strictly maintained below 5° C. The reaction mixture was diluted with 200 mL of dichloromethane and poured into 500 mL of water. The organic layer was washed successively with water (500 mL), saturated aqueous sodium bicarbonate solution (2×500 mL), and water (500 mL). The dichloromethane layer (of approximately 500 mL) containing crude 3-methylthio-1-propyl acrylate 18 was used directly in the following oxidation step.

The above dichloromethane layer was cooled in an ice bath and m-chloroperoxybenzoic acid (76.5 wt % average activity, 48.0 g, 278.2 mmol) was added in portions over a period of 75 minutes, while temperature was strictly maintained below 5° C. The progress of the reaction was monitored by TLC, and depending on amount of the remaining sulfide-acrylate present in the reaction mixture after 75 minutes, more m-chloroperoxybenzoic acid (2–5 g) was added. After a total reaction time of 2 hours at 0° C., the solvent was evaporated under reduced pressure, the obtained solid was extracted with deionized water (3×200 mL) and filtered. The filtrate was stirred with anion exchange resin (ca. 25 g, OH form) for one hour and filtered. The filtrate was evaporated under reduced pressure below 30+ C. to obtain crude compound 23 as a dark brownish-yellow oil (ca. 35 g). The crude product was purified by column chromatography (silica gel, solvents: hexane/ether, acetone; 45:45:10%) to give a colorless oil (30.1 g, 72.5 wt %) over two steps. Alternatively, the product was purified by vacuum distillation.

$^1$H NMR (200 MHZ, CDCl$_3$): δ6.40 (dd, J$_1$=17.2 Hz, J$_2$=1.7 Hz, 1H, olefinic), 6.09 (dd, J$_1$=17.2 Hz, J$_2$=10.4 Hz, 1H, olefinic), 5.83 (dd, J$_1$=10.4 Hz, J$_2$=1.7 Hz, 1H, olefinic), 4.30 (t, J=9.8 Hz, 2H, —CH$_2$CH$_2$O—), 2.76 (t, J=7.6 Hz, 2H, —CH$_2$CH$_2$SO—), 2.58 (s, 3H, CH$_3$SO—), 2.17 (m, 2H, —CH$_2$CH$_2$CH$_2$—); IR (Neat): 172.1, 1635, 1410, 1273, 1195 cm$^{-1}$; HRMS calcd for C$_7$H$_{13}$O$_3$S 177.058980, found 177.058541.

EXAMPLE 21

Synthesis of Methyl 3-(Acryloyloxy)Propyl Sulfone (26)

The same procedure as that used for the preparation of sulfoxide compound 23, described in Example 19, was used for preparation of compound 26, except that two equivalents of m-chloroperoxybenzoic acid rather than one equivalent were used.

3-methylthio-1-propyl acrylate (18) (8.11 g, 50.5 mmol), and m-chloroperoxybenzoic acid (9.34 g, 101.1 mmol) were reacted as described in Example 19. The crude product was purified by column chromatography (silica gel, 50 wt % ether/hexanes, ether) to give a clear oil compound 26 (6.7 g, 70 wt %), namely methyl 3-(acryloyloxy)propyl sulfone.

$^1$H NMR (200 MHZ, CDCl$_3$): δ6.39 (dd, J$_1$=17.2 Hz, J$_2$=1.5 Hz, 1H, olefinic), 6.08 (dd, J$_1$=17.2 Hz, J$_2$=10.2 Hz, 1H, olefinic), 5.84 (dd, J$_1$=10.2 Hz, J$_2$=1.7 Hz, 1H, olefinic), 4.27 (t, J=6.2 Hz, 2H, —CH$_2$CH$_2$O—), 3.09 (t, J=7.9 Hz, 2H, —CH$_2$CH$_2$SOO—), 2.90 (s, 3H, CH$_3$SOO—), 2.20 (m, 2H, —CH$_2$CH$_2$CH$_2$—); IR (Neat): 1718, 1635, 1411, 1297, 1193, 1132 cm$^{-1}$; HRMS calcd for C$_7$H$_{13}$O$_4$S 193.053456, found 193.053197.

EXAMPLE 22

Synthesis of 3-Methylthio-1-Propanol Tosylate

To a mixture of 3-methylthio-1-propanol (17) (5.0 g, 47.1 mmol), pyridine (7.43 g, 94.0 mmol) and CHCl$_3$ (47 mL) cooled in an ice bath, tosyl chloride (13.47 g, 70.6 mmol) was added in portions with stirring. The mixture was allowed to warm to room temperature after 1 hour and stirring was continued for an additional 15 hours. The mixture was diluted with CH$_2$Cl$_2$ (200 mL), washed with water (2×100 mL), and the organic phase as dried (Na$_2$SO$_4$). The solvent was evaporated and the resulting yellow oil purified by column chromatography (silica gel, 15 wt % ether/hexanes, 50 wt % ether/hexanes), to give a colorless oil (10.5 g, 86 wt %), namely 3-methylthio-1-propanol tosylate.

$^1$H NMR (200 MHZ, CDCl$_3$): δ7.78 (d, J=8.4 Hz, 2H, aromatic), 7.34 (d, J=8.1 Hz, 2H, aromatic), 4.13 (t, J=6.1 Hz, 2H, —CH$_2$CH$_2$O—), 2.50 (t, J=7.3 Hz, 2H, —CH$_2$CH$_2$S—), 2.44 (s, 3H, ArCH$_3$), 2.02 (s, 3H, CH$_3$S—), 1.91 (m, 2H, —CH$_2$CH$_2$CH$_2$—); IR (Neat): 1598, 1359, 1174 cm$^{-1}$.

EXAMPLE 23

Synthesis of 4,8-dithianonanol

To a mixture of 3-methylthio-1-propanol tosylate (14.14 g, 54.3 mmol), and 3-mercapto-1-propanol (5.0 g, 54.3 mmol) in dry THF (300 mL) was added potassium tert-butoxide (8.51 g, 80.0 mmol) in one portion under a blanket of nitrogen, and the resulting mixture was stirred at room temperature for 24 hours. Water (10 mL) was added drop-wise to the reaction mixture to quench excess potassium tert-butoxide, and solvent was evaporated under reduced pressure. The resulting solid was washed with ether (3×100 mL), and filtered. The ether layer was washed with water (3×100 mL) and dried (Na$_2$SO$_4$). Solvent evaporation produced 8.7 g of a light yellow oil. This product was used for acryloylation without further purification.

$^1$H NMR (200 MHZ, CDCl$_3$): δ3.75 (t, J=6.0 Hz, 2H, —CH$_2$OH), 2.61 (m, 6H, —CH$_2$CH$_2$S—), 2.09 (s, 3H, CH$_3$S—), 1.86 (m, 4H, —CH$_2$CH$_2$CH$_2$—), 1.69 (s, 1H, —CH$_2$OH); IR (Neat): 1435, 1257, 1024 cm$^{-1}$.

EXAMPLE 24

Synthesis of 4,8-Dithianonyl Acrylate

A procedure similar to the preparation described in Example 18 was followed. Compound 4,8-diathiononanol (8.65 g, 48.0 mmol), triethyl amine (7.3 g, 72.0 mmol), and acryloyl chloride (8.7 g, 96.1 mmol) were reacted to obtain 4,8-diathianonyl acrylate as a yellow oil (8.3 g) and used without further purification.

¹H NMR (200 MHZ, CDCl₃): δ6.48 (dd, J₁=15.7 Hz, J₂=1.6 Hz, 1H, olefinic), 6.13 (m, 1H, olefinic), 5.82 (d, J=9.1 Hz, 1H, olefinic), 4.25 (t, J=6.3 Hz, 2H, —CH₂CH₂O—), 2.61 (m, 6H, —CH₂CH₂S—), 2.09 (s, 3H, CH₃S—), 1.92 (m, 4H, —CH₂CH₂CH₂—); IR (Neat): 1729, 1635, 1407, 1267, 1190 cm⁻¹.

EXAMPLE 25

Synthesis of Methyl 3-(Acryloyloxy)Propyl Sulfide (25)

A procedure similar to that of the preparation described in Example 19 was used for preparation of compound 25.

Compound 4,8-dithianonyl acrylate (4.86 g, 20.7 mmol), and mCPBA (9.34 g, 41.4 mmol) were reacted as described in Example 18. The crude product was obtained as a clear oil that was purified by column chromatography (silica gel, 20 wt % acetone/ether, 50 wt % acetone/ether, acetone) to furnish a colorless oil that solidified upon standing in the refrigerator (3.4 g, 27 wt % over three steps from 5) to give compound 25, methyl 3-(acryloyloxy)propyl-sulfide.

¹H NMR (200 MHZ, CDCl₃): δ6.40 (dd, J₁=16.9 Hz, J₂=1.6 Hz, 1H, olefinic), 6.08 (dd, J₁=16.9 Hz, J₂=10.4 Hz, 1H, olefinic), 5.83 (dd, J₁=10.4 Hz, J₂=1.6 Hz, 1H, olefinic), 4.27 (t, J=6.4 Hz, 2H, —CH₂CH₂O—), 2.82 (m, 6H, —CH₂CH₂SO—), 2.58 (s, 3H, CH₃SO—), 2.33 (m, 2H, —CH₂CH₂CH₂SO—), 2.15 (m, 2H, —CH₂CH₂CH₂SO—); IR (Neat) : 1715, 1411, 1297, 1204 cm⁻¹; HRMS: calcd for C₁₀H₁₈O₄S₂ 266.064653, found 266.063869.

What is claimed is:

1. A soft contact lens fabricated from a hydrogel comprising an acrylamide functionalized carbohydrate monomer present in concentration from about 5 to about 40 wt % copolymerized with a hydrophilic or hydrophobic copolymerizing material selected from the group consisting of an acrylamide, methacrylamide, acrylate, methacrylate, siloxane and vinyl present in concentration from about 60 to about 95 wt %.

2. The lens of claim 1 wherein the copolymerizing material is N-vinyl-pyrrolidone, hydroxyethyl methacrylate, methyl methacrylate, methacrylic acid, glycerol methacrylate, 1,2-dihydroxypropyl methacrylate or N,N, dimethyl acrylamide.

3. The lens of claim 2 wherein the carbohydrate is selected from group consisting of compounds N-methyl-N-β-rhamnosylacrylamide, N-[3-(2-N'-ethyl propenamido) thiopropyl]-β-N-xylosyl acetamide; N-acryloyl-D-glucamine; N-acryloyl-N-methyl-D-glucamine; and N-acryloyl-N-(4(3,6,9-trioxa)decyloxybenzyl)-D-glucamine.

4. The lens of claim 3 wherein the carbohydrate is present in concentration from about 10 to about 20 wt %.

5. The lens of claim 4 wherein the carbohydrate is N-methyl-N-β-rhamnosyl acrylamide.

6. The lens of claim 4 wherein the carbohydrate is the N-[3-(2-N'-ethyl propenamido)thiopropyl]-β-N-xylosyl acetamide.

7. The lens of claim 4 wherein the carbohydrate is the N-acryloyl-D-glucamine.

8. The hydrogel of claim 4 wherein the carbohydrate is the N-acryloyl-N-methyl-D-glucamine.

9. The lens of claim 4 wherein the carbohydrate is the N-acryloyl-N-(4(3,6,9-trioxa)decyloxybenzyl)-D-glucamine.

* * * * *